US008372803B2

(12) United States Patent
Schnepf

(10) Patent No.: US 8,372,803 B2
(45) **Date of Patent: *Feb. 12, 2013**

(54) **MODIFIED *CRY*34 PROTEINS**

(75) Inventor: H. Ernest Schnepf, San Diego, CA (US)

(73) Assignee: Dow AgroSciences LLC, Indianapolis, IN (US)

( * ) Notice: Subject to any disclaimer, the term of this patent is extended or adjusted under 35 U.S.C. 154(b) by 739 days.

This patent is subject to a terminal disclaimer.

(21) Appl. No.: 12/422,743

(22) Filed: Apr. 13, 2009

(65) Prior Publication Data

US 2009/0205087 A1 Aug. 13, 2009

Related U.S. Application Data

(62) Division of application No. 10/956,725, filed on Oct. 1, 2004, now Pat. No. 7,524,810.

(60) Provisional application No. 60/508,567, filed on Oct. 3, 2003.

(51) Int. Cl.
*A01N 37/18* (2006.01)
*C07K 14/325* (2006.01)

(52) U.S. Cl. ........................................................ 514/4.5

(58) Field of Classification Search ........................ None
See application file for complete search history.

(56) References Cited

U.S. PATENT DOCUMENTS

| | | | |
|---|---|---|---|
| 6,083,499 | A | 7/2000 | Narva et al. |
| 6,127,180 | A | 10/2000 | Narva et al. |
| 6,218,188 | B1 | 4/2001 | Cardineau et al. |
| 6,372,480 | B1 | 4/2002 | Narva et al. |
| 6,677,148 | B1 | 1/2004 | Narva et al. |

FOREIGN PATENT DOCUMENTS

| | | |
|---|---|---|
| WO | WO 97/40162 | 10/1997 |
| WO | WO 98/23641 | 6/1998 |
| WO | WO 99/31248 | 6/1999 |
| WO | WO 00/66742 | 11/2000 |
| WO | WO 01/14417 | 3/2001 |
| WO | WO 03/018810 | 3/2003 |

OTHER PUBLICATIONS

Schnepf et al., Characterization of Cry34/Cry35 Binary Insecticidal Proteins from Diverse *Bacillus thuringiensis* Strain Collections. Applied and Environmental Microbiology (2005) 71(4): 1765-1774.
Ellis, R.T., et al., "Novel *Bacillus thuringiensis* Binary Insecticidal Crystal Proteins Active on Western . . .," Appl. Env. Microbio. (Mar. 2002), p. 1137-1145, vol. 68, Iss. 3.
Hofte, H. et al., "Insecticidal Crystal Proteins of *Bacillus thuringiensis*, " Microbiological Reviews (Jun. 1989), p. 242-255, vol. 53, No. 2.
Moellenbeck, D.J., et al., "Insecticidal Proteins from *Bacillus thuringiensis* Protect Corn from Corn Rootworms," Nature Biotechnology (Jul. 2001), pp. 668-672, vol. 19.
Voigt, C.A. et al., "Computational method to reduce the search space for directed protein evolution," Proc. Natl. Acad. Sci. U.S.A. (Mar. 27, 2001), p. 3778-83, vol. 98, No. 2.
Voigt, C.A. et al., "Computationally focusing the directed evolution of proteins," J. Cell Biochem. (2001), p. 58-63, Suppl. 37 (Abstract).

*Primary Examiner* — Anne Kubelik
(74) *Attorney, Agent, or Firm* — Ronald S. Maciak; Faegre Baker Daniels LLP

(57) ABSTRACT

This invention provides modified, insecticidal Cry34 proteins with enhanced properties as compared to wild-type Cry34 proteins. The modifications to these proteins were based in part on an analysis of the three-dimensional (3D) structure of this protein and other proteins in the Cry34 class. The subject invention also includes polynucleotides that encode these modified proteins, and transgenic plants that produce these modified proteins. This invention further provides methods of controlling plant pests, including rootworms, with these modified proteins. The modified proteins of the subject invention include chimeric toxins involving exchanged segments, domains, and motifs as discussed herein. The subject invention also provides methods of modifying Cry34 proteins.

3 Claims, 4 Drawing Sheets

SEQUENCE LISTING

<160> NUMBER OF SEQ ID NOS: 17

<210> SEQ ID NO 1
<211> LENGTH: 123
<212> TYPE: PRT
<213> ORGANISM: Bacillus thuringiensis

<400> SEQUENCE: 1

```
Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser Asn Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Phe Ala
65                  70                  75                  80

Gly Ser Asn Lys Tyr Asp Gly His Ser Asn Lys Ser Gln Tyr Glu Ile
                85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120
```

<210> SEQ ID NO 2
<211> LENGTH: 9
<212> TYPE: PRT
<213> ORGANISM: Artificial Sequence
<220> FEATURE:
<223> OTHER INFORMATION: dibasic residue

<400> SEQUENCE: 2

```
Met Lys Lys Ser Ala Arg Glu Val His
1               5
```

<210> SEQ ID NO 3
<211> LENGTH: 8
<212> TYPE: PRT
<213> ORGANISM: Artificial Sequence
<220> FEATURE:
<223> OTHER INFORMATION: dibasic residue

<400> SEQUENCE: 3

```
Met Lys Lys Ala Arg Glu Val His
1               5
```

<210> SEQ ID NO 4
<211> LENGTH: 7
<212> TYPE: PRT
<213> ORGANISM: Artificial Sequence
<220> FEATURE:
<223> OTHER INFORMATION: dibasic residue

<400> SEQUENCE: 4

```
Met Gly Gly Gly Ser Ala Arg
1               5
```

<210> SEQ ID NO 5
<211> LENGTH: 6
<212> TYPE: PRT
<213> ORGANISM: Artificial Sequence
<220> FEATURE:
<223> OTHER INFORMATION: dibasic residue

<400> SEQUENCE: 5

Met Gly Gly Gly Ala Arg
1 5

<210> SEQ ID NO 6
<211> LENGTH: 6
<212> TYPE: PRT
<213> ORGANISM: Artificial Sequence
<220> FEATURE:
<223> OTHER INFORMATION: dibasic residue

<400> SEQUENCE: 6

Met Ala Arg Glu Val His
1 5

<210> SEQ ID NO 7
<211> LENGTH: 5
<212> TYPE: PRT
<213> ORGANISM: Artificial Sequence
<220> FEATURE:
<223> OTHER INFORMATION: dibasic residue

<400> SEQUENCE: 7

Met Arg Glu Val His
1 5

<210> SEQ ID NO 8
<211> LENGTH: 4
<212> TYPE: PRT
<213> ORGANISM: Artificial Sequence
<220> FEATURE:
<223> OTHER INFORMATION: dibasic residue

<400> SEQUENCE: 8

Met Glu Val His
1

<210> SEQ ID NO 9
<211> LENGTH: 132
<212> TYPE: PRT
<213> ORGANISM: Bacillus thuringiensis

<400> SEQUENCE: 9

```
Met Ser Ala Arg Glu Val His Ile Glu Ile Ile Asn His Thr Gly His
1               5                   10                  15

Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Thr Leu His Phe Asp Asn Pro Tyr Ala
65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Val Gln Arg Asn Ile Ser Arg Tyr Thr Asn Lys Leu Cys
        115                 120                 125

Ser Asn Asn Ser
```

130

<210> SEQ ID NO 10
<211> LENGTH: 132
<212> TYPE: PRT
<213> ORGANISM: Bacillus thuringiensis

<400> SEQUENCE: 10

```
Met Ser Ala Arg Glu Val His Ile Glu Ile Ile Asn His Thr Gly His
1               5                   10                  15

Thr Leu Gln Met Asp Lys Arg Thr Arg Leu Ala His Gly Glu Trp Ile
            20                  25                  30

Ile Thr Pro Val Asn Val Pro Asn Asn Ser Ser Asp Leu Phe Gln Ala
        35                  40                  45

Gly Ser Asp Gly Val Leu Thr Gly Val Glu Gly Ile Ile Ile Tyr Thr
    50                  55                  60

Ile Asn Gly Glu Ile Glu Ile Pro Leu His Phe Asp Asn Pro Tyr Ala
65                  70                  75                  80

Gly Ser Asn Lys Tyr Ser Gly Arg Ser Ser Asp Asp Asp Tyr Lys Val
                85                  90                  95

Ile Thr Glu Ala Arg Ala Glu His Arg Ala Asn Asn His Asp His Val
            100                 105                 110

Thr Tyr Thr Val Gln Arg Asn Ile Ser Arg Tyr Thr Asn Lys Leu Cys
        115                 120                 125

Ser Asn Asn Ser
    130
```

<210> SEQ ID NO 11
<211> LENGTH: 119
<212> TYPE: PRT
<213> ORGANISM: Bacillus thuringiensis

<400> SEQUENCE: 11

```
Met Ser Ala Arg Glu Val His Ile Glu Ile Asn Asn Lys Thr Arg His
1               5                   10                  15

Thr Leu Gln Leu Glu Asp Lys Thr Lys Leu Ser Gly Gly Arg Trp Arg
            20                  25                  30

Thr Ser Pro Thr Asn Val Ala Arg Asp Thr Ile Lys Thr Phe Val Ala
        35                  40                  45

Glu Ser His Gly Phe Met Thr Gly Val Glu Gly Ile Ile Tyr Phe Ser
    50                  55                  60

Val Asn Gly Asp Ala Glu Ile Ser Leu His Phe Asp Asn Pro Tyr Ile
65                  70                  75                  80

Gly Ser Asn Lys Cys Asp Gly Ser Ser Asp Lys Pro Glu Tyr Glu Val
                85                  90                  95

Ile Thr Gln Ser Gly Ser Gly Asp Lys Ser His Val Thr Tyr Thr Ile
            100                 105                 110

Gln Thr Val Ser Leu Arg Leu
        115
```

<210> SEQ ID NO 12
<211> LENGTH: 119
<212> TYPE: PRT
<213> ORGANISM: Bacillus thuringiensis

<400> SEQUENCE: 12

```
Met Ser Ala Arg Glu Val His Ile Glu Ile Asn Asn Lys Thr Arg His
1               5                   10                  15
```

Thr Leu Gln Leu Glu Asp Lys Thr Lys Leu Ser Gly Gly Arg Trp Arg
20 25 30

Thr Ser Pro Thr Asn Val Ala Arg Asp Thr Ile Lys Thr Phe Val Ala
35 40 45

Glu Ser His Gly Phe Met Thr Gly Val Glu Gly Ile Ile Tyr Phe Ser
50 55 60

Val Asn Gly Asp Ala Glu Ile Ser Leu His Phe Asp Asn Pro Tyr Ile
65 70 75 80

Gly Ser Asn Lys Cys Asp Gly Ser Ser Asp Lys Pro Glu Tyr Glu Val
85 90 95

Ile Thr Gln Ser Gly Ser Gly Asp Lys Ser His Val Thr Tyr Thr Ile
100 105 110

Gln Thr Val Ser Leu Arg Leu
115

<210> SEQ ID NO 13
<211> LENGTH: 119
<212> TYPE: PRT
<213> ORGANISM: Bacillus thuringiensis

<400> SEQUENCE: 13

Met Ser Ala Arg Glu Val His Ile Glu Ile Asn Asn Lys Thr Arg His
1 5 10 15

Thr Leu Gln Leu Glu Asp Lys Thr Lys Leu Ser Gly Gly Arg Trp Arg
20 25 30

Thr Ser Pro Thr Asn Val Ala Arg Asp Thr Ile Lys Thr Phe Val Ala
35 40 45

Glu Ser His Gly Phe Met Thr Gly Val Glu Gly Ile Ile Tyr Phe Ser
50 55 60

Val Asn Gly Asp Ala Glu Ile Ser Leu His Phe Asp Asn Pro Tyr Ile
65 70 75 80

Gly Ser Asn Lys Cys Asp Gly Ser Ser Asp Lys Pro Glu Tyr Glu Val
85 90 95

Ile Thr Gln Ser Gly Ser Gly Asp Lys Ser His Val Thr Tyr Thr Ile
100 105 110

Gln Thr Val Ser Leu Arg Leu
115

<210> SEQ ID NO 14
<211> LENGTH: 123
<212> TYPE: PRT
<213> ORGANISM: Bacillus thuringiensis

<400> SEQUENCE: 14

Met Ser Ala Arg Glu Val His Ile Asp Val Asn Asn Lys Thr Gly His
1 5 10 15

Thr Leu Gln Leu Glu Asp Lys Thr Lys Leu Asp Gly Gly Arg Trp Arg
20 25 30

Thr Ser Pro Thr Asn Val Ala Asn Asp Gln Ile Lys Thr Phe Val Ala
35 40 45

Glu Ser His Gly Phe Met Thr Gly Thr Glu Gly Thr Ile Tyr Tyr Ser
50 55 60

Ile Asn Gly Glu Ala Glu Ile Ser Leu Tyr Phe Asp Asn Pro Tyr Ser
65 70 75 80

Gly Ser Asn Lys Tyr Asp Gly His Ser Asn Lys Pro Gln Tyr Glu Val
85 90 95

Thr Thr Gln Gly Gly Ser Gly Asn Gln Ser His Val Thr Tyr Thr Ile

```
            100                 105                 110

Gln Thr Ala Ser Ser Arg Tyr Gly Asn Asn Ser
        115                 120


<210> SEQ ID NO 15
<211> LENGTH: 123
<212> TYPE: PRT
<213> ORGANISM: Bacillus thuringiensis

<400> SEQUENCE: 15

Met Ser Ala Arg Glu Val His Ile Asp Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Tyr Ser
65                  70                  75                  80

Gly Ser Asn Lys Tyr Asp Gly His Ser Asn Lys Asn Gln Tyr Glu Val
                85                  90                  95

Ile Thr Gln Gly Gly Ser Gly Asn Gln Ser His Val Thr Tyr Thr Ile
            100                 105                 110

Gln Thr Val Ser Ser Arg Tyr Gly Asn Asn Ser
        115                 120


<210> SEQ ID NO 16
<211> LENGTH: 123
<212> TYPE: PRT
<213> ORGANISM: Bacillus thuringiensis

<400> SEQUENCE: 16

Met Ser Ala Arg Glu Val His Ile Asn Val Asn Asn Lys Thr Gly His
1               5                   10                  15

Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser His Gly Phe Met Thr Gly Thr Glu Gly His Ile Tyr Tyr Ser
    50                  55                  60

Ile Asn Gly Glu Ala Glu Ile Ser Leu Tyr Phe Asp Asn Pro Tyr Ser
65                  70                  75                  80

Gly Ser Asn Lys Tyr Asp Gly Asp Ser Asn Lys Pro Gln Tyr Glu Val
                85                  90                  95

Thr Thr Gln Gly Gly Ser Gly Asn Gln Ser His Val Thr Tyr Thr Ile
            100                 105                 110

Gln Thr Ala Ser Ser Arg Tyr Gly Asn Asn Ser
        115                 120


<210> SEQ ID NO 17
<211> LENGTH: 123
<212> TYPE: PRT
<213> ORGANISM: Bacillus thuringiensis

<400> SEQUENCE: 17

Met Ser Ala Arg Glu Val His Ile Asp Val Asn Asn Lys Thr Gly His
1               5                   10                  15
```

-continued

```
Thr Leu Gln Leu Glu Asp Lys Thr Lys Leu Asp Gly Gly Arg Trp Arg
            20                  25                  30

Thr Ser Pro Thr Asn Val Ala Asn Asp Gln Ile Lys Thr Phe Val Ala
        35                  40                  45

Glu Ser Asn Gly Phe Met Thr Gly Thr Glu Gly Thr Ile Tyr Tyr Ser
    50                  55                  60

Ile Asn Gly Glu Ala Glu Ile Ser Leu Tyr Phe Asp Asn Pro Phe Ala
65                  70                  75                  80

Gly Ser Asn Lys Tyr Asp Gly His Ser Asn Lys Ser Gln Tyr Glu Ile
                85                  90                  95

Ile Thr Gln Gly Gly Ser Gly Asn Gln Ser His Val Thr Tyr Thr Ile
            100                 105                 110

Gln Thr Thr Ser Ser Arg Tyr Gly His Lys Ser
        115                 120
```

MODIFIED *CRY*34 PROTEINS

CROSS-REFERENCE TO A RELATED APPLICATION

The present application is a divisional of U.S. Ser. No. 10/956,725, filed Oct. 1, 2004, which claims benefit to Provisional Application Ser. No. 60/508,567, filed Oct. 3, 2003, which are hereby incorporated by reference herein in their entirety, including any figures, tables, nucleic acid sequences, amino acid sequences, or drawings.

BACKGROUND OF THE INVENTION

Coleopterans are a significant group of agricultural pests that cause extensive damage to crops each year. Examples of coleopteran pests include corn rootworm and alfalfa weevils. Additional notable examples include Colorado potato beetle, boll weevil, and Japanese beetle.

Insecticidal crystal proteins from some strains of *Bacillus thuringiensis* (B.t.) are well-known in the art. See, e.g., Höfte et al., *Microbial Reviews*, Vol. 53, No. 2, pp. 242-255 (1989). These proteins are typically produced by the bacteria as approximately 130 kDa protoxins that are then cleaved by proteases in the insect midgut, after ingestion by the insect, to yield a roughly 60 kDa core toxin. These proteins are known as crystal proteins because distinct crystalline inclusions can be observed with spores in some, strains of B.t. These crystalline inclusions are often composed of several distinct proteins.

A new insecticidal protein system was discovered in *Bacillus thuringiensis* as disclosed in WO 97/40162. This system comprises two proteins—one of approximately 15 kDa and the other of about 45 kDa. See also U.S. Pat. Nos. 6,083,499 and 6,127,180. These proteins have now been assigned to their own classes, and accordingly received the Cry designations of Cry34 and Cry35, respectively. See Crickmore et al. website (biols.susx.ac.uk/home/Neil_Crickmore/Bt/). Many other related proteins of this type of system have now been disclosed. See e.g. U.S. Pat. No. 6,372,480; WO 01/14417; and WO 00/66742. Plant-optimized genes that encode such proteins, wherein the genes are engineered to use codons for optimized expression in plants, have also been disclosed. See e.g. U.S. Pat. No. 6,218,188.

Details of the three-dimensional structure of these proteins have not, heretofore, been disclosed. With information regarding the three-dimensional structures of these proteins, it would be possible to rationally design modifications to the natural, bacterial proteins to improve various desirable characteristics of these proteins. Having and analyzing the 3D structure of a protein can be highly advantageous for focusing or restricting directed evolution and improvement programs.

However, obtaining purified crystals of B.t. insect toxins has been a difficult process (although some examples do exist; see e.g. WO 98/23641 and WO 99/31248). It has been difficult to obtain purified crystals of adequate quality. For example, there has been a tendency for these proteins to form aggregates that are not suitable for refinement of the structure to high resolution. In addition, B.t. has been an inferior protein producer for the level and quality of protein required for X-ray crystallography and related biochemical purposes. Frequent protease contamination has also been an associated obstacle. Still further, native B.t. strains typically produce crystals having a mixture of proteins; thus, there have been some issues with isolating and purifying single protein types from such mixtures (to the degree required for sophisticated analysis).

BRIEF SUMMARY OF THE INVENTION

This invention provides modified, insecticidal Cry34 proteins with enhanced properties as compared to wild-type Cry34 proteins. The modifications to these proteins as discussed below were based in part on an analysis of the three-dimensional (3D) structure of the ~15 kDa 149B1 protein and other proteins in the Cry34 class. The subject invention also includes polynucleotides that encode these modified proteins, and transgenic plants that produce these modified proteins. This invention further provides methods of controlling plant pests, including rootworms, with these modified proteins.

The modified proteins of the subject invention include chimeric toxins involving exchanged segments, domains, and motifs as discussed herein.

The subject invention also provides methods of modifying Cry34 proteins. However, the modifications described herein can be applied to other (structurally similar) proteins and peptides as well.

BRIEF DESCRIPTION OF THE SEQUENCES

Figure 1A:
FIGS. 1A and 1B illustrate the basic three-dimensional structure of typical Cry34 proteins.

SEQ ID NO:1 is the amino acid sequence of the wild-type 149B1 ~15 kDa (Cry 34Ab1) protein.

SEQ ID NO:2 is an example of a dibasic residue truncation or modification to improve activity according to the subject invention.

SEQ ID NO:3 is an example of a dibasic residue truncation or modification to improve activity according to the subject invention.

SEQ ID NO:4 is an example of a dibasic residue truncation or modification to improve activity according to the subject invention.

SEQ ID NO:5 is an example of a dibasic residue truncation or modification to improve activity according to the subject invention.

SEQ ID NO:6 is an example of using a run of glycines to reduce effect of Met1 hydrophobicity.

SEQ ID NO:7 is an example of using a run of glycines to reduce effect of Met1 hydrophobicity.

SEQ ID NO:8 is an example of using a run of glycines to reduce effect of Met1 hydrophobicity.

SEQ ID NO:9 is the Cry34 protein designated PS201HH2.

SEQ ID NO:10 is the Cry34 protein designated PS201L3.

SEQ ID NO:11 is the Cry34 protein designated PS185GG.

SEQ ID NO:12 is the Cry34 protein designated PS69Q.

SEQ ID NO:13 is the Cry34 protein designated PS80JJ1.

SEQ ID NO:14 is the Cry34 protein designated KR1369.

SEQ ID NO:15 is the Cry34 protein designated PS167H2.

SEQ ID NO:16 is the Cry34 protein designated PS158×10.

SEQ ID NO:17 is the Cry34 protein designated PS149B1.

BRIEF DESCRIPTION OF THE APPENDICES

Appendix 1 provides the atomic coordinates for the 149B1 Cry34 protein.

Appendix 2 is a spreadsheet that includes accessibility information regarding the amino acid residues of Cry34Ab1.

DETAILED DESCRIPTION

This invention provides modified, insecticidal Cry34 proteins with enhanced properties as compared to wild-type Cry34 proteins. The modifications to these proteins as discussed below were based in part on analysis of the three-dimensional (3D) structure of the ~15 kDa 149B1 protein and other proteins in the Cry34 class, together with other analytic approaches. The subject invention also includes polynucleotides that encode these modified proteins, and transgenic plants that produce these modified proteins, and seeds and other plant materials (such as pollen and germplasm) produced by such plants. This invention further provides methods of controlling plant pests, including rootworms, by using these modified proteins.

As referred to herein, Cry34-M proteins are any proteins modified or produced synthetically (that differ from wild-type Cry34 proteins) according to the methods disclosed and/or suggested herein.

Synthetic proteins of the subject invention include Cry34-M proteins with increased stability in plants and/or increased activity against insects.

Some synthetic proteins of the subject invention have one or more amino acid substitutions that improve binding, protease resistance (in plants, for example) and/or susceptibility (in insect guts, for example), hydrophobicity/hydrophilicity, charge distribution, and like characteristics of the synthetic proteins as compared to wild-type Cry34 proteins.

Some synthetic proteins of the subject invention are the result of modifying one or more amino acid residues of a given wild-type Cry34 protein (a Cry34A protein, for example) to make the resulting synthetic sequence more or less like that of a different wild-type Cry34 protein (a Cry34B protein, for example). This approach was based in part on substituting residues based on sequence diversity in homologous protein toxins together with analyzing the corresponding crystal structure.

The modified proteins of the subject invention include chimeric toxins involving exchanged domains and motifs as discussed herein.

Further proteins of the subject invention are obtainable by focused sequence shuffling or site saturation mutagenesis, wherein said shuffling is directed, as described herein, to certain regions or segments of Cry34 proteins.

Still further, proteins of the subject invention include those that were obtained in part by using computational molecular evolution based in part on structural data. That is, while sequence alignments/comparisons of various Cry34 proteins can provide some clues as to differences between given proteins in this class, sequence alignments alone are not able to convey similar structural motifs that might be shared by various proteins, including Cry34-class proteins.

The subject invention includes methods of modifying at least one amino acid residue of a Cry34 protein, including the step of consulting a three-dimensional model of a Cry34 protein.

Atomic coordinates for the 149B1 Cry34 protein are provided in Appendix 1.

Basic Structure of Cry34 Proteins

Figure 1B:
Figure 2A:
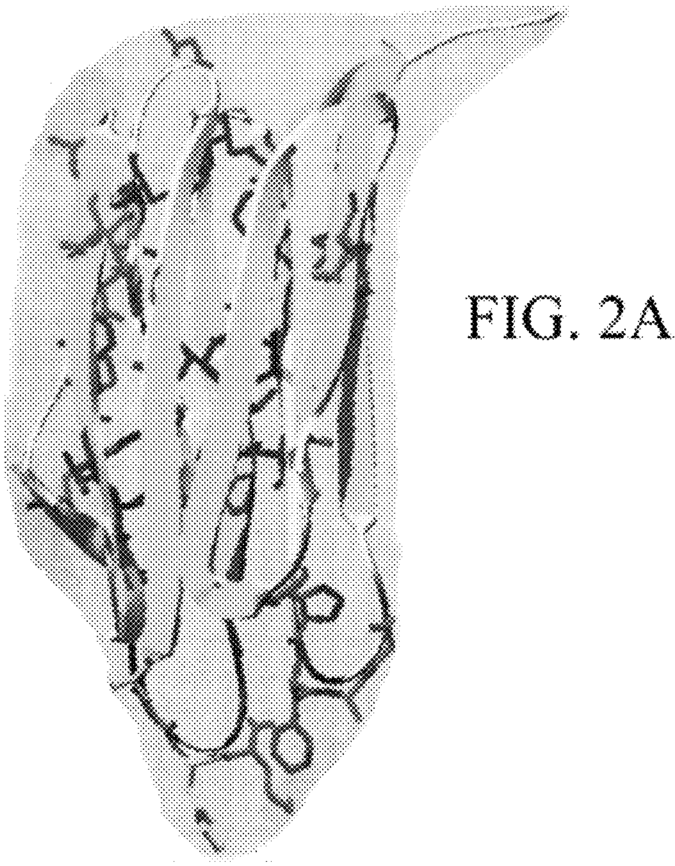
FIGS. 2A and 2B provide an illustration of the three-dimensional structure of typical Cry34 proteins, with some surface-exposed residues indicated.
Figure 2B:
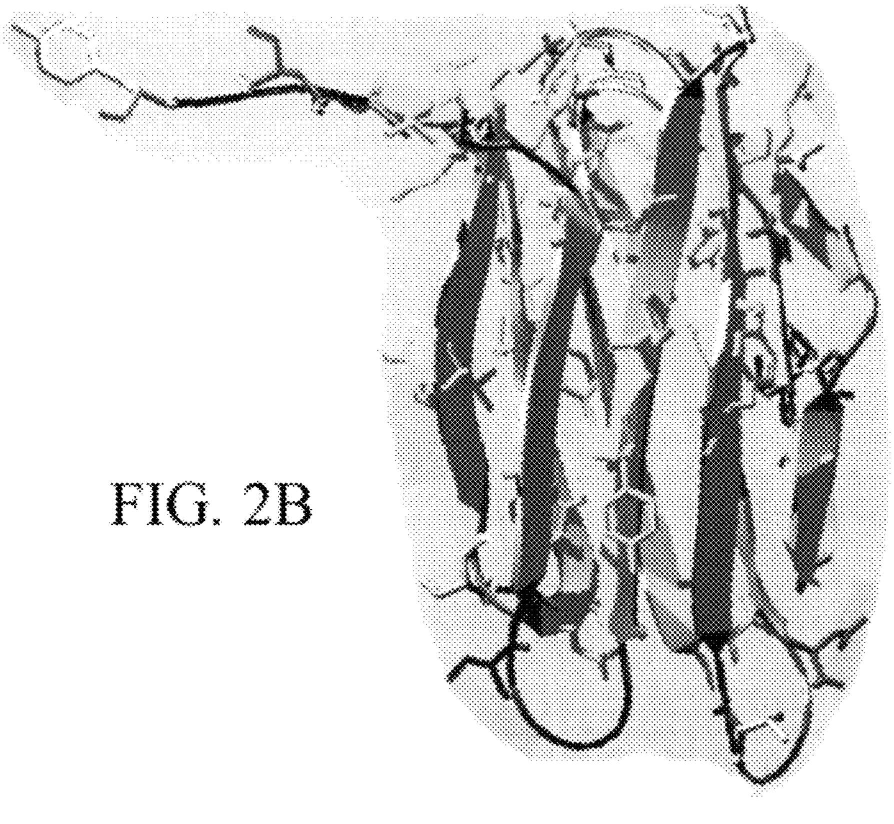
Figure 3A:
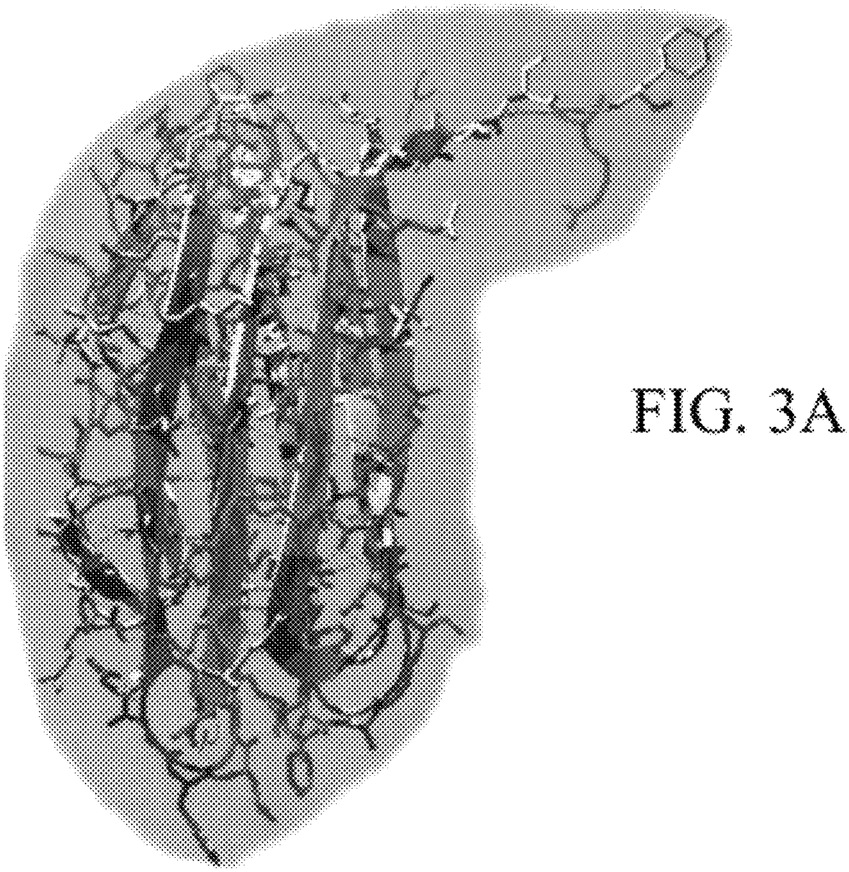
FIGS. 3A and 3B illustrate surface-exposed residues with an additional level of detail, and can also be used to show the two main domains of Cry34 molecules.
Figure 3B:
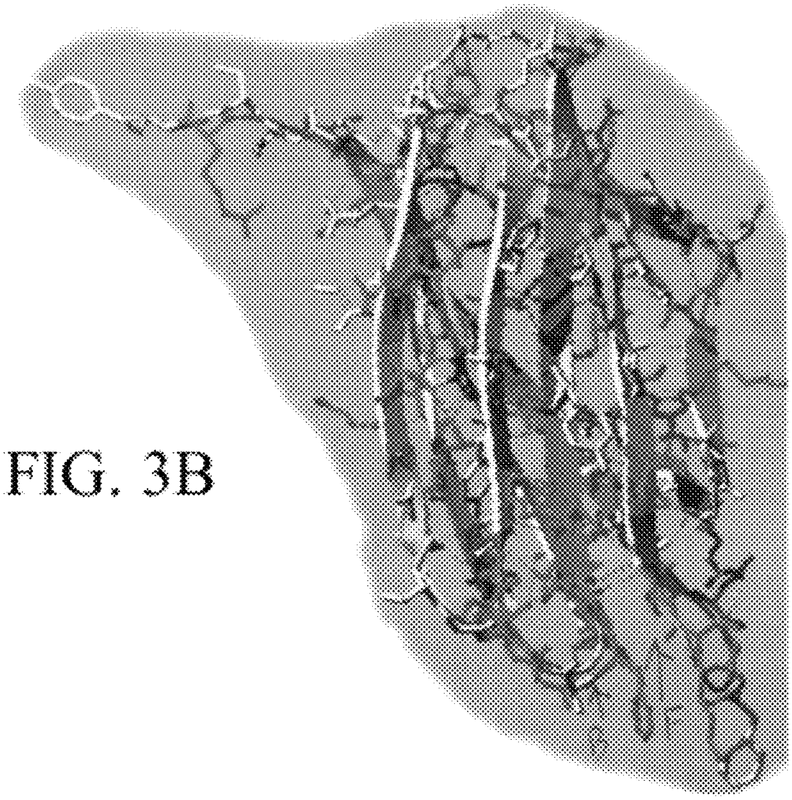

FIGS. 1A and 1B illustrate the basic structure of the Cry34 proteins. FIGS. 2A and 2B illustrate a further level, with some surface-exposed residues indicated in the illustration. FIGS. 3A and 3B provide a still further detailed illustration. FIGS. 3A and 3B basically suggest that the molecule is in two modules: a front subdomain (approximately residues 1-67) and a back subdomain (residues ~67-end). As discussed below in Example 6, this also suggests that the subdomain boundary would be a good place to make chimerics.

Before discussing the various structural features and overall structure of the Cry34 molecules, it should be noted that "~" used before a range of numbers (e.g., ~1-9) signifies that this is an approximate range of residues (unless otherwise specified). Thus, ~1-9 means the same as ~1-9 unless otherwise indicated. Some examples of overlapping segment definitions can be found herein.

The overall structure of Cry34 molecules can be summarized as follows. Some residues omitted at the ends (residues ~1-2 and ~120-123) are assumed to be a part of the amino acid chain in the crystals, but they are too variable in position to be fixed in the model.

| Strand # or loop | amino acid residues of segment | location/orientation on FIG. 1 |
|---|---|---|
| 1 | ~4-13 | bottom-top |
| Loop | ~14-18 | top |
| 2a, 2b | ~19-21; 25-27 | top-bottom |
| Loop | ~28, 29 | bottom |
| 3 | ~30-32 | bottom-top |
| coil | 33-41 | bottom-top |
| Loop | ~39-41 | top |
| 4 | ~42-50 | top-bottom |
| 4-5 loop | ~51-56 | bottom |
| 5 | ~57-65 | bottom-top |
| Loop | ~66-68 | top |
| 6 | ~69-77 | top-bottom |
| 6-7 loop | ~78-83 | bottom |
| 7 | ~84-90 | bottom-top |
| Loop | ~91-92 | top |
| 8 | ~93-101 | top-bottom |
| Loop | ~102-103 | bottom |
| 9 | ~104-115 | bottom-top |
| coil | 116-119 | top |
| coil | 120-123 | top - not observed in crystal |

Residues ~1-9 form a beta strand running (N terminus to C terminal direction) from the bottom to top of the Cry34 molecule as illustrated in FIG. 1. A loop occurs at residues ~14-18 (at the top of the molecule as illustrated in FIG. 1) followed by strand 2 (residues ~19-21; 25-27), consisting of two short beta strands, which runs downward as illustrated in FIG. 1.

This is followed by another loop at residues ~28-29 (bottom FIG. 1). Residues ~30-41 form a segment (running back up the molecule of FIG. 1) consisting of a short beta strand (30-32) and a less structured segment (33-41).

Segment ~42-50 is a beta strand running (N->C) back down the molecule as shown in FIG. 1.

The large loop, at the bottom of the molecule of FIG. 1, extending from residues ~50-57 is very interesting. This is discussed in more detail below.

The ~58-68 segment runs back to top of molecule (as illustrated in FIG. 1) where there is a loop at residues ~66-70.

The ~70-78 segment (strand 6) runs back down to the ~78-81 loop. The ~81-91 segment (strand 7) transitions into a ~91-95 loop at the top of the molecule of FIG. 1.

Strands 6-7 are involved with the formation of a center pore, as discussed in more detail below. As such, the inward-facing residues in these strands are preferably not modified. Similarly, the ~76-80 loop is preferably not modified.

The ~95-102 segment travels back down the molecule to a "bottom" loop at residues ~102-106.

The segment of residues ~106-114 travels back up the molecule and ends at the carboxy terminus at ~123, after the protruding tail at the top left of the molecule of FIG. 1 (after residue ~114).

Possible Mechanisms of Action of Cry34 Proteins

The Cry35 protein is known to act with the Cry34 (~15 kDa) protein. The 3D structure of the Cry35 protein is discussed in more detail in U.S. Ser. No. 60/508,637 entitled, "Modified Cry35 Proteins." Without being limited by any one theory, the Cry34 protein could bind to a multimeric association of assembled Cry35 proteins via a cross-subunit binding site. This would explain the inability of Cry34/35 to form associations in vitro in initial observations. (Thus, it appears unlikely that a membrane-bound Cry35 monomer associates with the membrane and then with the 14 kDa as a binding partner.) It would be consistent with other known, similar protein models if the Cry35 multimer associates with the cellular membrane and embeds using a beta-hairpin-based membrane interaction domain. Upon multimerization, this could form a beta-barrel-like assembly of the Cry35 subunits—usually seven. (The beta hairpin of Cry35 is from residues ~238-262, centered at 254 and 255, and is structurally similar to other proposed hairpins for other known proteins. Although sequence similarity with those proteins is weak, there is structural similarity, which also suggests that the bottom loops, especially ~78-83, embed in the membrane.) The multimer would then facilitate entry of the 15 kDa protein, which could have a cellular target via binding, or could form pores on its own (i.e. beta-barrel type via a loop of residues ~28-~55).

It appears that the Cry34 protein could insert into insect cell membranes. One manner in which this could occur, based on various molecular and energetic analyses discussed herein, is via "16-39 unfolding." "Hinging out" of the segment comprising strands 2-3 would expose the hydrophobic core of this protein to the membrane surface. Strands 2-3 can thus be thought of as the bar of a hand grenade, which springs out when it is not depressed. While not being limited by a single theory regarding an exact mechanism of action, one possibility is that multiple ~15 kDa proteins could associate and form a channel in this manner. As illustrated, and in this model, the C-terminal tail sticks straight up and could bind the ~45 kDa (Cry35).

A second model involves residues 27-53 (strands 3-4). This model is interesting because the 3∃ strands are long enough to span the membrane. Although the remainder of the molecule in this conformation does not appear to be very stable, the 30-50 segment could fold onto the other sheet.

Yet another model involves residues ~15-56 (strands 2-3 and 3-4). This is a more variable portion of the sequence in the Cry34 family, especially residues ~27-53 (strands 3-4). One option is to modify a residue in this segment to turn it into an amphipathic ∀-helix. The stretch from residues ~42-57 has a distinct ∀/∃ hydrophobic moment. It is also possible to observe some alpha helical amphipathic character on helical wheel slots of the 30-53/55 stretch.

In any case, the loops between strands 2 and 3 (residues 28-29) and 4 and 5 (residues 51-56) are key hinges.

For residues that are identified herein as being ideal for substitution, conservative changes can be made as defined below in Example 8. However, in some cases, nonconservative changes would be preferred. The efficacy of such changes can be initially analyzed using computer modeling such as Voigt, C. A., Mayo, S. L., Arnold, F. H., and Wang, Z. G., "Computationally focusing the directed evolution of proteins," *J. Cell Biochem.* (2001), Suppl. 37:58-63; and Voigt, C. A., Mayo, S. L., Arnold, F. H., and Wang, Z. G., "Computational method to reduce the search space for directed protein evolution," *Proc. Natl. Acad. Sci. U.S.A.* (Mar. 27, 2001), 98(7):3778-83. Techniques for producing and confirming the activity of proteins modified accordingly are well-known in the art.

Figure 4:
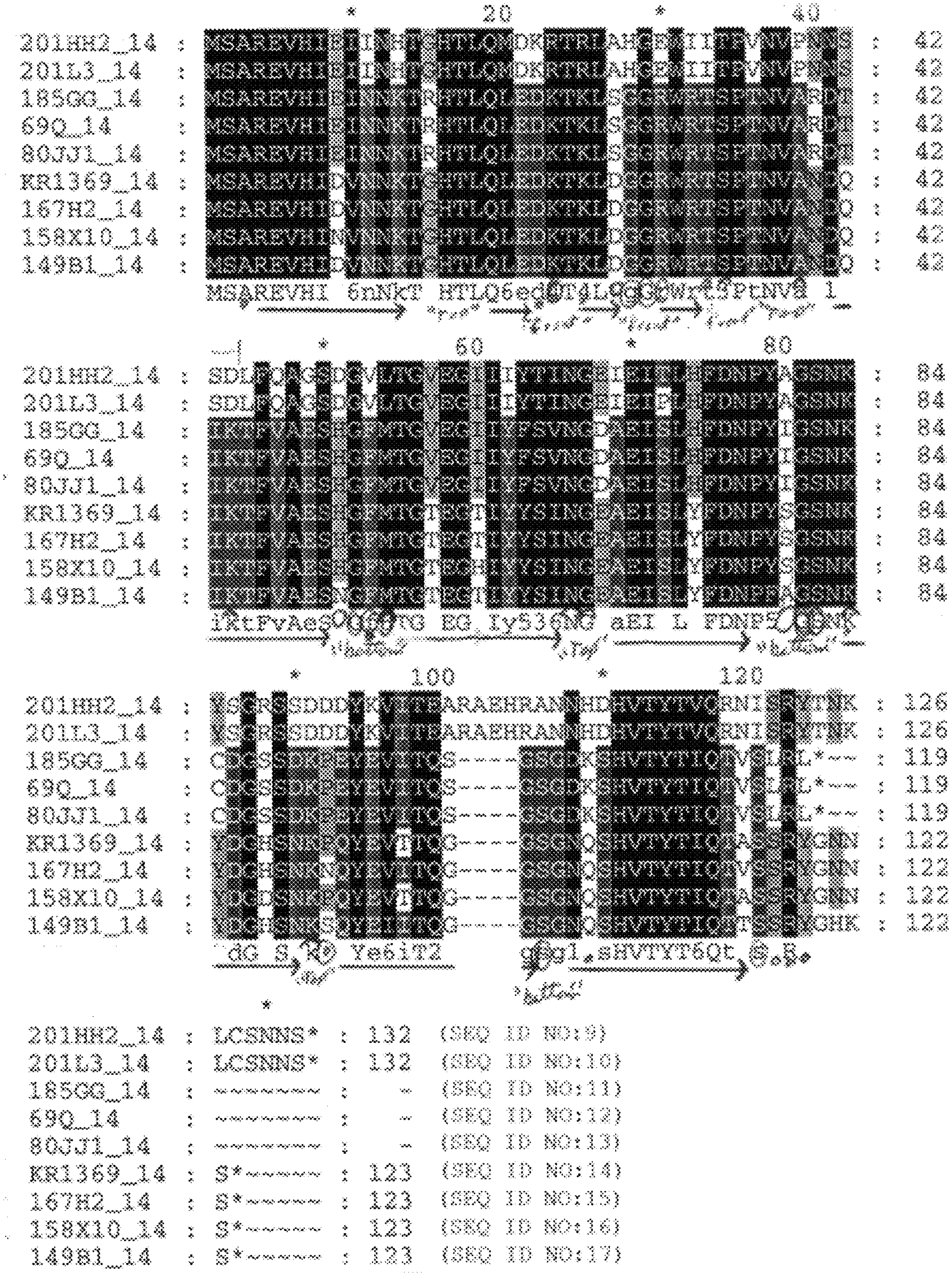
FIG. 4 shows a multiple sequence alignment of various Cry34 proteins.

It should be understood that while the specific residue numbers referred to herein relate primarily to the exemplified 149B1 protein, the subject disclosure shows that all Cry34 proteins have similar structures to those exemplified herein. Thus, as one skilled in the art would know, with the benefit of this disclosure, corresponding residues and segments are now identifiable in the other Cry34 proteins. Thus, the specific examples for the 149B1 protein can be applied to the other proteins in the Cry34 family. The exact numbering of the residues might not strictly correspond to the 149B1 protein, but the corresponding residues are readily identifiable in light of the subject disclosure. See, e.g., FIG. 4.

Unless indicated otherwise herein, all known Cry34 wild-type proteins appear to have the same basic structure, although there are some important differences in their amino acid residues at certain positions. The sequences of various Cry34 proteins and genes are described in various patent and other references as indicated below (such sequences can be used according to some embodiments of the subject invention): For example, the following protein sequences can be used according to the subject invention:

| Cry designation | Source isolate | GENBANK Acc. No. |
|---|---|---|
| 34Aa1 | PS80JJ1 | AAG50341 |
| 34Aa2 | EG5899 | AAK64560 |
| 34Ab1 | PS149B1 | AAG41671 |
| 34Ac1 | PS167H2 | AAG50118 |
| 34Ac2 | EG9444 | AAK64562 |
| 34Ba1 | EG4851 | AAK64566 |

35Aa1, 35Ab1, and 35Ac1 are also disclosed in WO 01/14417 as follows.

| Source isolate | SEQ ID NO: IN WO 01/14417 |
|---|---|
| PS80JJ1 | 32 |
| PS167H2 | 36 |
| PS149B1 | 41 |

There are many additional Cry34 sequences disclosed in WO 01/14417 that can be used according to the subject invention. For example:

| Source isolate | SEQ ID NO: IN WO 01/14417 |
|---|---|
| PS131W2 | 52 |
| PS158T3 | 56 |
| PS158X10 | 60 |
| PS185FF | 62 |
| PS185GG | 66 |

-continued

| Source isolate | SEQ ID NO: IN WO 01/14417 |
|---|---|
| PS185L12 | 70 |
| PS185W3 | 72 |
| PS186FF | 74 |
| PS187F3 | 76 |
| PS187L14 | 84 |
| PS187Y2 | 88 |
| PS204G4 | 100 |
| PS204I11 | 102 |
| PS204J7 | 104 |
| PS236B6 | 106 |
| PS242K10 | 108 |
| PS246P42 | 112 |
| PS69Q | 114 |
| KB54 | 118 |
| KR1209 | 120 |
| KR1369 | 122 |
| KR589 | 124 |
| PS201L3 | 134 |
| PS187G1 | 138 |
| PS201HH2 | 142 |
| KR1369 | 146 |
| PS137A | 150 |
| PS201V2 | 152 |
| PS207C3 | 154 |

Several other source isolates are also disclosed in WO 01/14417. The PS designation of the source isolate can be dropped for ease of reference when referring to a protein obtainable from that isolate. Various polynucleotides that encode these proteins are also known in the art and disclosed in various references cited herein.

All patents, patent applications, provisional applications, and publications referred to or cited herein are incorporated by reference in their entirety to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Modification of Surface-Exposed Residues

The following table lists exposed residues and the degree to which they are exposed:

| Residue # | Degree of exposure |
|---|---|
| 3 | some exposure |
| 22 | some exposure |
| 23 | outward-facing side chain |
| 25 | some exposure |
| 27 | outward-facing side chain |
| 28 | outward-facing side chain |
| 29 | outward facing side chain |
| 30 | outward facing side chain |
| 33 | more exposed |
| 34 | more exposed |
| 39 | more exposed |
| 44 | more exposed |
| 51 | outward-facing side chain |
| 52 | outward-facing side chain |
| 53 | outward-facing side chain/some exposure |
| 54 | outward-facing side chain/more exposed |
| 66 | more exposed |
| 67 | more exposed |
| 80 | outward-facing side chain |

-continued

| Residue # | Degree of exposure |
|---|---|
| 81 | outward-facing side chain |
| 82 | outward-facing side chain |
| 83 | more exposed/some exposure |
| 91 | more exposed |
| 92 | some exposure in outward-facing side chain |
| 102 | outward-facing side chain |
| 105 | some exposure |
| 116 | outward-facing side chain |
| 117 | some exposure |
| 118 | some exposure |
| 119 | some exposure |

In general, these residues (especially those that are "more exposed" and "outward facing") are preferred for modification and would have little impact on the overall structure of the molecule. That is, if function is affected, the modification of function would be due most likely to the alteration of the (exposed) side chain, as opposed to a propagated structure distortion elsewhere.

Example 2

Modification of Exposed Loops and "Charged Girdle" Modifications to Improve Solubility A "charged girdle" can be identified above the hydrophobic bottom loops. Histidines in the "girdle" can be changed to R or K to improve solubility. Likewise, the "T" at position 60 can be changed to H, K, or R (or E). Following are other examples of changes that can be made to improve the solubility of the molecule:

H7R, H16R, H88R, H107R, and N51H.

Alternatively, an H7Y modification can be for improved stability. Thus, preferred Cry35-M proteins have histidine residues modified to R or K.

Another possibility is V47 (an outward facing hydrophobic residue) to H,K,R, or more generally to I, M, L, T, A, K, H, or R.

Preferably, for all of the modifications suggested herein (in this Example and elsewhere throughout), single changes would be made first, and then multiple changes would be made—combining the single modifications that result in equal or better activity.

Example 3

Scanning-Based Changes

Appendix 2 provides data that was analyzed to determine residues that would be good to change, based on similarity value (less is better), accessibility (more is better), outward facing side chain (more is better), and B-factor (how well fixed the residues are in the crystal structure (more is better). Using the table of Appendix 1, accessible residues with high B-factors (i.e. >30 in last column) were initially identified, then accessible residues with scores of 1 & 2, then outfacing with high B-factor, then outfacing score 2, and then those with an outfacing score of 1. Substitutions can follow those found in the different families, prioritized by profile similarity (substitutions column), etc.

Example 4

Nearest Neighbor Analysis

A nearest neighbor analysis of the first 55 residues was conducted. H-bonds from residue 56 and higher were also identified that: 1) connect to 16-36, and 2) are between sheets (68-89 connecting to 94-110). This analysis indicated that the residues past 56 were more interconnected by H-bonds than the earlier segment. Residues S34 and N51 do not have non-adjacent neighbors and should be highly substitutable. That is, S34 and N51 have minimal contacts aside from adjacent residues and should be highly substitutable. Changing S34 is preferred.

Example 5

Analysis of Force-Field Energies

An analysis was conducted of force-field energies and threading energy rankings. Higher energies relative to the electron density data could indicate stress on the protein that could aid unfolding. Segments 20-24, 33-36 and 43-44 are potentially stressed and worthy of modification. By using this design, one can obtain a molecule that behaves normally but "unfolds" easier when desired.

Example 6

Construction of Chimerics

Chimerics can be constructed according to the subject invention to assess functionality, preferably residues 66/67 as the crossover point, and preferably using the 201 L3 14 kDa gene (as the 201L3 14 kDa is much less active, this can show which of the segmental sequence differences disclosed herein are responsible, as well as where large numbers of changes are tolerated). Additional chimerics with, for example, 80JJ1 and 158×10 can also be constructed to assess activity and stability effects.

Chimerics of the subject invention can also be truncated as explained below in Example 7. These combinations can be constructed to assess the effects of different (or omitted or truncated) homolog C-termini, including the effects of charge and polarity changes. Thus, preferred chimerics are of the 1-66/67-end type.

Example 7

Terminal Deletions to Produce Truncated Cry 34 Proteins

5' and 3' deletions can be performed to make N- and C-terminally truncated proteins. The essential minimum coding segment can be determined in this manner.

In addition, as plant-produced protein is minus Met1, improvement of activity could be obtained from N-terminal truncation or modifications with, e.g., dibasic residues (e.g. MKKSAREVH (SEQ ID NO.:2) . . . , MKKAREVH (SEQ ID NO.:3) . . . , or MGGGSAR (SEQ ID NO.:4) . . . , MGGGAR (SEQ ID NO.:5). . . ) to enhance cleavage to get S2 or A3 at the N-terminus. Alternatively, the subject invention includes the use of a run of glycines to reduce effect of Men hydrophobicity. A3 or R4 appear to be critical, so the truncations would encode MAREVH (SEQ ID NO.:6) . . . , MREVH (SEQ ID NO.:7), MEVH (SEQ ID NO.:8) . . . , etc. until activity is drastically affected.

3' deletions can also be constructed, and the criticality of the tail can be assessed. Residues prior to T114 appear to be critical, so terminal truncations of whole segments could advantageously be made, rather than processively from the 3' end one at a time. These techniques can also be used to determine the functionality of family variability in the C-termini (T114 on), as much of this may be totally dispensible.

Alternatively, the C-terminus can be retained, but crossover chimerics can be constructed in this region to improve activity. In the Cry34 family, there are several sequence variants in this region with only an Arg (R118) totally conserved. One example of this type of variant would consist of the 149B1 sequence through T114, then 80JJ1 sequence (for example) could be used at the terminus. Various combinations of this type could be constructed using any of the Cry34 family members.

Truncations that exhibit improved activity or other functionality or characteristics can also be used with further approaches to modification and improvement as discussed above and elsewhere herein (and vice versa).

Example 8

Analyzing Multiple Sequence Alignments

Thus, according to the guidance provided herein, one can align and compare the sequences of any or all known Cry34 homologues. One alignment of some Cry34 alleles is shown in FIG. 5. Chemical properties of the residues can be compared in such an alignment, and then related to the 3D structure. This type of combined analysis can now be conducted.

Another method of the subject invention is to, for example, introduce any one or more or all possible changes observed (from such alignments) in the other related Cry34 proteins to the Cry 34Ab1 protein, for example, if these changes are in regions of the protein that would tolerate change, based on an analysis of the 3D structure of the proteins as disclosed herein. Conversely, the subject invention includes making the 201L3 protein more like another Cry 34 protein, such as the 149B1 Cry 34 protein, if these changes are in regions of the protein that would tolerate change, based on an analysis of the 3D structure of the proteins as disclosed herein. The 201L3 binary toxins are the most divergent, by sequence, and are also less active than the 149B1 binary toxins; however, the 201L3 14 kDa protein, for example, is more susceptible to protease processing than is the 149B1 protein.

Unless otherwise indicated, sequences were aligned using ClustalW default parameters at the ClustalW WWW Service at the European Bioinformatics Institute website (ebi.ac.uk/clustalw). Various sequence analysis software is available for displaying various alignments, including the free Genedoc package available at (psc.edu/biomed/genedoc/). Multiple sequence alignments can be analyzed using two Genedoc functions:

Conservation mode produces a display that emphasizes the degree of conservation in each column in the alignment. Positions with 60, 80 or 100% identity, for example, can be shaded in different grayscale tones. Residue similarity scoring can be enabled, such that residue similarity groups (Blossum 62) are given arbitrary numbers on the consensus line.

Chemical properties highlights sequence residues that share a defined set of properties. In this analysis default shading can be used to highlight the following groups by color:

| negatively charged | positively charged | amide | alcohol | aliphatic | aromatic | small | sulfur | other |
|---|---|---|---|---|---|---|---|---|
| D, E | H, K, R | N, Q | S, T | L, I, V | F, Y, W | A, G | M, C | P |

Residue substitutions can be identified by scanning the length of the sequence alignment. Thus, one can align the sequences of various Cry34 proteins and look for "outlying" amino acids (residues that are different, i.e. of a different chemical class, as compared to others at a corresponding position).

Again, the 149B1 and 201L3 Cry34 proteins are good reference points, in part because the 149B1 Cry34/Cry35 combination is one of the most active binary toxin combinations (wild-type) known to date. On the other hand, the 201L3 Cry34/Cry35 combination is one of the most active binary toxin combinations (wild-type) known to date.

Using the atomic coordinates and guidance provided herein, one can conduct molecular modeling with other residue substitutions at the nonconserved positions to probe the toxin for improvements. One can engineer changes to introduce amino acid residues with other chemically different side groups, such as opposite polarity, opposite charge, or bulky versus small.

Example 9

Focused Sequence Shuffling or Site Saturation Mutagenesis

The subject disclosure of the 3D structure of Cry 34 proteins will now make site- or region-directed "gene shuffling" much easier and more efficient. U.S. Pat. No. 5,605,793, for example, describes methods for generating additional molecular diversity by using DNA reassembly after random fragmentation. Evolutionarily conserved residues in critical regions of the protein can now be avoided in attempting molecular evolution by shuffling or site saturation mutagenesis. This type of "shuffling" and molecular evolution can now be focused on segments, and nonconserved residues for example, in ideal regions as discussed above.

APPENDIX 1

```
CRYST1   100.561   100.561   56.196 90.00 90.00 90.00 I 4 2 2
SCALE1   0.009944 0.000000 0.000000      0.00000
SCALE2   0.000000 0.009944 0.000000      0.00000
SCALE3   0.000000 0.000000 0.017795      0.00000
ATOM      1  N    ALA  A   3   −20.201   5.256   −9.776  1.00  30.71 N
ATOM      2  CA   ALA  A   3   −20.306   6.536   −9.021  1.00  31.43 C
ATOM      3  CB   ALA  A   3   −21.512   6.515   −8.090  1.00  30.94 C
ATOM      4  C    ALA  A   3   −19.038   6.895   −8.247  1.00  31.22 C
ATOM      5  O    ALA  A   3   −18.999   6.807   −7.019  1.00  31.41 O
ATOM      6  N    ARG  A   4   −17.991   7.259   −8.981  1.00  30.93 N
ATOM      7  CA   ARG  A   4   −16.810   7.859   −8.382  1.00  30.72 C
ATOM      8  CB   ARG  A   4   −15.587   7.664   −9.303  1.00  31.38 C
ATOM      9  CG   ARG  A   4   −15.357   6.217   −9.816  1.00  32.08 C
ATOM     10  CD   ARG  A   4   −14.418   5.337   −8.967  1.00  35.83 C
ATOM     11  NE   ARG  A   4   −14.950   3.979   −8.834  1.00  38.50 N
ATOM     12  CZ   ARG  A   4   −14.524   3.071   −7.960  1.00  41.72 C
ATOM     13  NH1  ARG  A   4   −13.531   3.345   −7.125  1.00  41.86 N
ATOM     14  NH2  ARG  A   4   −15.098   1.874   −7.926  1.00  41.83 N
ATOM     15  C    ARG  A   4   −17.225   9.349   −8.279  1.00  30.38 C
ATOM     16  O    ARG  A   4   −18.053   9.783   −9.072  1.00  28.33 O
ATOM     17  N    GLU  A   5   −16.762  10.109   −7.280  1.00  30.19 N
ATOM     18  CA   GLU  A   5   −16.964  11.581   −7.297  1.00  29.80 C
ATOM     19  CB   GLU  A   5   −18.057  12.043   −6.326  1.00  30.75 C
ATOM     20  CG   GLU  A   5   −19.037  10.967   −5.902  1.00  37.70 C
ATOM     21  CD   GLU  A   5   −19.818  11.356   −4.662  1.00  44.27 C
ATOM     22  OE1  GLU  A   5   −20.273  12.516   −4.578  1.00  47.47 O
ATOM     23  OE2  GLU  A   5   −19.978  10.501   −3.770  1.00  49.26 O
ATOM     24  C    GLU  A   5   −15.634  12.299   −6.981  1.00  29.00 C
ATOM     25  O    GLU  A   5   −14.779  11.719   −6.320  1.00  29.94 O
ATOM     26  N    VAL  A   6   −15.443  13.531   −7.468  1.00  25.81 N
ATOM     27  CA   VAL  A   6   −14.223  14.315   −7.179  1.00  25.07 C
ATOM     28  CB   VAL  A   6   −13.332  14.549   −8.419  1.00  23.55 C
ATOM     29  CG1  VAL  A   6   −12.082  15.345   −8.037  1.00  24.08 C
ATOM     30  CG2  VAL  A   6   −12.941  13.236   −9.051  1.00  22.59 C
ATOM     31  C    VAL  A   6   −14.602  15.673   −6.604  1.00  23.69 C
ATOM     32  O    VAL  A   6   −15.278  16.467   −7.258  1.00  24.63 O
ATOM     33  N    HIS  A   7   −14.185  15.927   −5.370  1.00  20.84 N
ATOM     34  CA   HIS  A   7   −14.494  17.190   −4.725  1.00  20.66 C
ATOM     35  CB   HIS  A   7   −14.888  16.993   −3.269  1.00  20.78 C
ATOM     36  CG   HIS  A   7   −16.146  16.205   −3.080  1.00  20.91 C
ATOM     37  ND1  HIS  A   7   −17.291  16.752   −2.542  1.00  21.69 N
ATOM     38  CE1  HIS  A   7   −18.233  15.827   −2.483  1.00  23.78 C
ATOM     39  NE2  HIS  A   7   −17.738  14.699   −2.959  1.00  24.50 N
ATOM     40  CD2  HIS  A   7   −16.434  14.908   −3.338  1.00  18.03 C
ATOM     41  C    HIS  A   7   −13.263  18.053   −4.824  1.00  20.90 C
ATOM     42  O    HIS  A   7   −12.151  17.613   −4.535  1.00  21.83 O
ATOM     43  N    ILE  A   8   −13.469  19.295   −5.226  1.00  20.16 N
ATOM     44  CA   ILE  A   8   −12.355  20.164   −5.517  1.00  22.63 C
ATOM     45  CB   ILE  A   8   −12.343  20.450   −7.028  1.00  23.00 C
ATOM     46  CG1  ILE  A   8   −12.156  19.142   −7.797  1.00  23.32 C
ATOM     47  CD1  ILE  A   8   −12.773  19.146   −9.168  1.00  23.46 C
ATOM     48  CG2  ILE  A   8   −11.264  21.454   −7.384  1.00  23.14 C
ATOM     49  C    ILE  A   8   −12.403  21.457   −4.741  1.00  23.55 C
ATOM     50  O    ILE  A   8   −13.375  22.206   −4.814  1.00  24.73 O
ATOM     51  N    ASP  A   9   −11.349  21.705   −3.977  1.00  21.78 N
ATOM     52  CA   ASP  A   9   −11.206  22.976   −3.300  1.00  22.57 C
ATOM     53  CB   ASP  A   9   −10.816  22.787   −1.835  1.00  22.71 C
```

APPENDIX 1-continued

| | | | | | | | | | | | |
|---|---|---|---|---|---|---|---|---|---|---|---|
| ATOM | 54 | CG | ASP | A | 9 | −12.010 | 22.500 | −0.946 | 1.00 | 26.20 | C |
| ATOM | 55 | OD1 | ASP | A | 9 | −12.961 | 21.845 | −1.418 | 1.00 | 27.39 | O |
| ATOM | 56 | OD2 | ASP | A | 9 | −12.086 | 22.892 | 0.237 | 1.00 | 24.89 | O |
| ATOM | 57 | C | ASP | A | 9 | −10.153 | 23.796 | −4.031 | 1.00 | 23.03 | C |
| ATOM | 58 | O | ASP | A | 9 | −9.042 | 23.325 | −4.279 | 1.00 | 23.74 | O |
| ATOM | 59 | N | VAL | A | 10 | −10.522 | 25.011 | −4.410 | 1.00 | 22.83 | N |
| ATOM | 60 | CA | VAL | A | 10 | −9.580 | 25.927 | −5.025 | 1.00 | 23.02 | C |
| ATOM | 61 | CB | VAL | A | 10 | −10.088 | 26.460 | −6.378 | 1.00 | 24.93 | C |
| ATOM | 62 | CG1 | VAL | A | 10 | −9.120 | 27.485 | −6.946 | 1.00 | 24.64 | C |
| ATOM | 63 | CG2 | VAL | A | 10 | −10.281 | 25.310 | −7.359 | 1.00 | 22.94 | C |
| ATOM | 64 | C | VAL | A | 10 | −9.361 | 27.061 | −4.032 | 1.00 | 23.75 | C |
| ATOM | 65 | O | VAL | A | 10 | −10.308 | 27.743 | −3.637 | 1.00 | 22.37 | O |
| ATOM | 66 | N | ASN | A | 11 | −8.117 | 27.220 | −3.591 | 1.00 | 23.28 | N |
| ATOM | 67 | CA | ASN | A | 11 | −7.761 | 28.273 | −2.648 | 1.00 | 23.15 | C |
| ATOM | 68 | CB | ASN | A | 11 | −7.074 | 27.696 | −1.408 | 1.00 | 23.76 | C |
| ATOM | 69 | CG | ASN | A | 11 | −6.896 | 28.726 | −0.306 | 1.00 | 20.01 | C |
| ATOM | 70 | OD1 | ASN | A | 11 | −7.244 | 29.895 | −0.471 | 1.00 | 21.29 | O |
| ATOM | 71 | ND2 | ASN | A | 11 | −6.354 | 28.294 | 0.827 | 1.00 | 19.05 | N |
| ATOM | 72 | C | ASN | A | 11 | −6.874 | 29.293 | −3.346 | 1.00 | 23.41 | C |
| ATOM | 73 | O | ASN | A | 11 | −5.729 | 29.009 | −3.700 | 1.00 | 20.46 | O |
| ATOM | 74 | N | ASN | A | 12 | −7.429 | 30.482 | −3.542 | 1.00 | 22.15 | N |
| ATOM | 75 | CA | ASN | A | 12 | −6.771 | 31.558 | −4.268 | 1.00 | 22.11 | C |
| ATOM | 76 | CB | ASN | A | 12 | −7.845 | 32.400 | −4.966 | 1.00 | 21.40 | C |
| ATOM | 77 | CG | ASN | A | 12 | −7.272 | 33.515 | −5.823 | 1.00 | 23.16 | C |
| ATOM | 78 | OD1 | ASN | A | 12 | −5.953 | 33.602 | −5.892 | 1.00 | 23.90 | O |
| ATOM | 79 | ND2 | ASN | A | 12 | −8.020 | 34.289 | −6.422 | 1.00 | 20.48 | N |
| ATOM | 80 | C | ASN | A | 12 | −5.926 | 32.445 | −3.366 | 1.00 | 21.36 | C |
| ATOM | 81 | O | ASN | A | 12 | −6.460 | 33.241 | −2.598 | 1.00 | 20.68 | O |
| ATOM | 82 | N | LYS | A | 13 | −4.607 | 32.306 | −3.453 | 1.00 | 21.06 | N |
| ATOM | 83 | CA | LYS | A | 13 | −3.712 | 33.185 | −2.709 | 1.00 | 21.88 | C |
| ATOM | 84 | CB | LYS | A | 13 | −2.816 | 32.379 | −1.759 | 1.00 | 21.33 | C |
| ATOM | 85 | CG | LYS | A | 13 | −3.542 | 31.342 | −0.909 | 1.00 | 25.03 | C |
| ATOM | 86 | CD | LYS | A | 13 | −4.573 | 31.977 | 0.009 | 1.00 | 20.87 | C |
| ATOM | 87 | CE | LYS | A | 13 | −3.922 | 32.813 | 1.095 | 1.00 | 20.40 | C |
| ATOM | 88 | NZ | LYS | A | 13 | −4.940 | 33.342 | 2.044 | 1.00 | 22.73 | N |
| ATOM | 89 | C | LYS | A | 13 | −2.840 | 34.024 | −3.659 | 1.00 | 21.42 | C |
| ATOM | 90 | O | LYS | A | 13 | −1.736 | 34.419 | −3.292 | 1.00 | 21.14 | O |
| ATOM | 91 | N | THR | A | 14 | −3.341 | 34.324 | −4.858 | 1.00 | 22.35 | N |
| ATOM | 92 | CA | THR | A | 14 | −2.524 | 34.996 | −5.885 | 1.00 | 23.71 | C |
| ATOM | 93 | CB | THR | A | 14 | −3.071 | 34.723 | −7.305 | 1.00 | 23.77 | C |
| ATOM | 94 | OG1 | THR | A | 14 | −4.405 | 35.238 | −7.417 | 1.00 | 20.92 | O |
| ATOM | 95 | CG2 | THR | A | 14 | −3.218 | 33.248 | −7.566 | 1.00 | 21.29 | C |
| ATOM | 96 | C | THR | A | 14 | −2.330 | 36.502 | −5.796 | 1.00 | 24.19 | C |
| ATOM | 97 | O | THR | A | 14 | −1.368 | 37.031 | −6.349 | 1.00 | 23.92 | O |
| ATOM | 98 | N | GLY | A | 15 | −3.250 | 37.204 | −5.152 | 1.00 | 24.50 | N |
| ATOM | 99 | CA | GLY | A | 15 | −3.187 | 38.651 | −5.153 | 1.00 | 25.75 | C |
| ATOM | 100 | C | GLY | A | 15 | −4.230 | 39.180 | −6.119 | 1.00 | 27.59 | C |
| ATOM | 101 | O | GLY | A | 15 | −4.530 | 40.372 | −6.131 | 1.00 | 28.57 | O |
| ATOM | 102 | N | HIS | A | 16 | −4.800 | 38.284 | −6.922 | 1.00 | 27.52 | N |
| ATOM | 103 | CA | HIS | A | 16 | −5.810 | 38.679 | −7.899 | 1.00 | 28.11 | C |
| ATOM | 104 | CB | HIS | A | 16 | −5.189 | 38.775 | −9.295 | 1.00 | 27.98 | C |
| ATOM | 105 | CG | HIS | A | 16 | −3.840 | 39.423 | −9.311 | 1.00 | 30.05 | C |
| ATOM | 106 | ND1 | HIS | A | 16 | −3.670 | 40.791 | −9.333 | 1.00 | 33.09 | N |
| ATOM | 107 | CE1 | HIS | A | 16 | −2.379 | 41.072 | −9.339 | 1.00 | 34.00 | C |
| ATOM | 108 | NE2 | HIS | A | 16 | −1.705 | 39.937 | −9.322 | 1.00 | 32.89 | N |
| ATOM | 109 | CD2 | HIS | A | 16 | −2.595 | 38.890 | −9.303 | 1.00 | 28.62 | C |
| ATOM | 110 | C | HIS | A | 16 | −7.012 | 37.735 | −7.931 | 1.00 | 27.80 | C |
| ATOM | 111 | O | HIS | A | 16 | −7.064 | 36.747 | −7.199 | 1.00 | 28.85 | O |
| ATOM | 112 | N | THR | A | 17 | −7.979 | 38.060 | −8.784 | 1.00 | 26.58 | N |
| ATOM | 113 | CA | THR | A | 17 | −9.172 | 37.241 | −8.969 | 1.00 | 26.56 | C |
| ATOM | 114 | CB | THR | A | 17 | −10.325 | 38.111 | −9.507 | 1.00 | 27.04 | C |
| ATOM | 115 | OG1 | THR | A | 17 | −10.830 | 38.950 | −8.461 | 1.00 | 29.48 | O |
| ATOM | 116 | CG2 | THR | A | 17 | −11.522 | 37.249 | −9.876 | 1.00 | 28.65 | C |
| ATOM | 117 | C | THR | A | 17 | −8.884 | 36.119 | −9.961 | 1.00 | 25.23 | C |
| ATOM | 118 | O | THR | A | 17 | −8.191 | 36.331 | −10.954 | 1.00 | 25.39 | O |
| ATOM | 119 | N | LEU | A | 18 | −9.390 | 34.927 | −9.678 | 1.00 | 24.46 | N |
| ATOM | 120 | CA | LEU | A | 18 | −9.256 | 33.819 | −10.610 | 1.00 | 24.42 | C |
| ATOM | 121 | CB | LEU | A | 18 | −9.209 | 32.475 | −9.857 | 1.00 | 23.82 | C |
| ATOM | 122 | CG | LEU | A | 18 | −7.941 | 32.093 | −9.094 | 1.00 | 27.31 | C |
| ATOM | 123 | CD1 | LEU | A | 18 | −8.110 | 30.747 | −8.402 | 1.00 | 24.27 | C |
| ATOM | 124 | CD2 | LEU | A | 18 | −6.752 | 32.065 | −10.035 | 1.00 | 26.11 | C |
| ATOM | 125 | C | LEU | A | 18 | −10.419 | 33.778 | −11.591 | 1.00 | 23.64 | C |
| ATOM | 126 | O | LEU | A | 18 | −11.542 | 33.510 | −11.172 | 1.00 | 22.96 | O |
| ATOM | 127 | N | GLN | A | 19 | −10.171 | 34.100 | −12.844 | 1.00 | 22.79 | N |
| ATOM | 128 | CA | GLN | A | 19 | −11.257 | 34.088 | −13.816 | 1.00 | 22.92 | C |
| ATOM | 129 | CB | GLN | A | 19 | −11.084 | 35.181 | −14.858 | 1.00 | 22.29 | C |
| ATOM | 130 | CG | GLN | A | 19 | −10.820 | 36.536 | −14.284 | 1.00 | 22.38 | C |
| ATOM | 131 | CD | GLN | A | 19 | −10.602 | 37.562 | −15.364 | 1.00 | 25.21 | C |
| ATOM | 132 | OE1 | GLN | A | 19 | −10.134 | 37.231 | −16.453 | 1.00 | 26.18 | O |
| ATOM | 133 | NE2 | GLN | A | 19 | −10.942 | 38.809 | −15.076 | 1.00 | 21.40 | N |

APPENDIX 1-continued

| | | | | | | | | | | | |
|---|---|---|---|---|---|---|---|---|---|---|---|
| ATOM | 134 | C | GLN | A | 19 | −11.377 | 32.758 | −14.529 | 1.00 | 22.81 | C |
| ATOM | 135 | O | GLN | A | 19 | −10.475 | 32.337 | −15.251 | 1.00 | 24.12 | O |
| ATOM | 136 | N | LEU | A | 20 | −12.511 | 32.108 | −14.327 | 1.00 | 23.53 | N |
| ATOM | 137 | CA | LEU | A | 20 | −12.802 | 30.860 | −14.996 | 1.00 | 24.65 | C |
| ATOM | 138 | CB | LEU | A | 20 | −14.196 | 30.404 | −14.586 | 1.00 | 23.85 | C |
| ATOM | 139 | CG | LEU | A | 20 | −14.667 | 29.047 | −15.086 | 1.00 | 27.91 | C |
| ATOM | 140 | CD1 | LEU | A | 20 | −13.802 | 27.955 | −14.487 | 1.00 | 26.97 | C |
| ATOM | 141 | CD2 | LEU | A | 20 | −16.123 | 28.858 | −14.712 | 1.00 | 30.71 | C |
| ATOM | 142 | C | LEU | A | 20 | −12.759 | 31.069 | −16.507 | 1.00 | 24.96 | C |
| ATOM | 143 | O | LEU | A | 20 | −13.321 | 32.037 | −17.017 | 1.00 | 25.48 | O |
| ATOM | 144 | N | GLU | A | 21 | −12.084 | 30.173 | −17.222 | 1.00 | 26.38 | N |
| ATOM | 145 | CA | GLU | A | 21 | −12.059 | 30.236 | −18.682 | 1.00 | 26.52 | C |
| ATOM | 146 | CB | GLU | A | 21 | −10.668 | 29.928 | −19.217 | 1.00 | 26.85 | C |
| ATOM | 147 | CG | GLU | A | 21 | −9.580 | 30.870 | −18.748 | 1.00 | 34.03 | C |
| ATOM | 148 | CD | GLU | A | 21 | −8.240 | 30.479 | −19.322 | 1.00 | 37.96 | C |
| ATOM | 149 | OE1 | GLU | A | 21 | −8.102 | 29.305 | −19.717 | 1.00 | 42.56 | O |
| ATOM | 150 | OE2 | GLU | A | 21 | −7.337 | 31.336 | −19.389 | 1.00 | 40.28 | O |
| ATOM | 151 | C | GLU | A | 21 | −13.049 | 29.247 | −19.290 | 1.00 | 26.33 | C |
| ATOM | 152 | O | GLU | A | 21 | −13.276 | 28.169 | −18.742 | 1.00 | 26.34 | O |
| ATOM | 153 | N | ASP | A | 22 | −13.616 | 29.611 | −20.437 | 1.00 | 25.94 | N |
| ATOM | 154 | CA | ASP | A | 22 | −14.594 | 28.770 | −21.126 | 1.00 | 27.04 | C |
| ATOM | 155 | CB | ASP | A | 22 | −15.094 | 29.466 | −22.392 | 1.00 | 25.88 | C |
| ATOM | 156 | CG | ASP | A | 22 | −15.960 | 30.661 | −22.091 | 1.00 | 30.27 | C |
| ATOM | 157 | OD1 | ASP | A | 22 | −16.582 | 30.683 | −21.009 | 1.00 | 32.86 | O |
| ATOM | 158 | OD2 | ASP | A | 22 | −16.080 | 31.627 | −22.873 | 1.00 | 27.23 | O |
| ATOM | 159 | C | ASP | A | 22 | −14.053 | 27.401 | −21.510 | 1.00 | 26.65 | C |
| ATOM | 160 | O | ASP | A | 22 | −14.807 | 26.432 | −21.602 | 1.00 | 26.69 | O |
| ATOM | 161 | N | LYS | A | 23 | −12.747 | 27.325 | −21.741 | 1.00 | 26.01 | N |
| ATOM | 162 | CA | LYS | A | 23 | −12.123 | 26.081 | −22.182 | 1.00 | 26.49 | C |
| ATOM | 163 | CB | LYS | A | 23 | −10.722 | 26.345 | −22.713 | 1.00 | 26.21 | C |
| ATOM | 164 | CG | LYS | A | 23 | −9.753 | 26.862 | −21.689 | 1.00 | 27.33 | C |
| ATOM | 165 | CD | LYS | A | 23 | −8.601 | 27.489 | −22.417 | 1.00 | 33.65 | C |
| ATOM | 166 | CE | LYS | A | 23 | −7.295 | 27.221 | −21.733 | 1.00 | 34.50 | C |
| ATOM | 167 | NZ | LYS | A | 23 | −6.199 | 27.485 | −22.695 | 1.00 | 34.21 | N |
| ATOM | 168 | C | LYS | A | 23 | −12.104 | 24.982 | −21.122 | 1.00 | 25.01 | C |
| ATOM | 169 | O | LYS | A | 23 | −11.767 | 23.836 | −21.415 | 1.00 | 23.79 | O |
| ATOM | 170 | N | THR | A | 24 | −12.457 | 25.343 | −19.894 | 1.00 | 24.23 | N |
| ATOM | 171 | CA | THR | A | 24 | −12.602 | 24.384 | −18.806 | 1.00 | 24.49 | C |
| ATOM | 172 | CB | THR | A | 24 | −13.241 | 25.106 | −17.608 | 1.00 | 23.78 | C |
| ATOM | 173 | OG1 | THR | A | 24 | −12.229 | 25.839 | −16.904 | 1.00 | 26.18 | O |
| ATOM | 174 | CG2 | THR | A | 24 | −13.753 | 24.123 | −16.578 | 1.00 | 24.17 | C |
| ATOM | 175 | C | THR | A | 24 | −13.471 | 23.210 | −19.286 | 1.00 | 25.27 | C |
| ATOM | 176 | O | THR | A | 24 | −14.544 | 23.429 | −19.849 | 1.00 | 24.35 | O |
| ATOM | 177 | N | LYS | A | 25 | −13.017 | 21.974 | −19.074 | 1.00 | 25.29 | N |
| ATOM | 178 | CA | LYS | A | 25 | −13.725 | 20.814 | −19.630 | 1.00 | 27.09 | C |
| ATOM | 179 | CB | LYS | A | 25 | −13.248 | 20.551 | −21.075 | 1.00 | 27.03 | C |
| ATOM | 180 | CG | LYS | A | 25 | −13.952 | 19.382 | −21.788 | 1.00 | 30.39 | C |
| ATOM | 181 | CD | LYS | A | 25 | −13.731 | 19.362 | −23.313 | 1.00 | 33.98 | C |
| ATOM | 182 | CE | LYS | A | 25 | −12.458 | 18.611 | −23.723 | 1.00 | 36.91 | C |
| ATOM | 183 | NZ | LYS | A | 25 | −12.478 | 18.122 | −25.142 | 1.00 | 33.14 | N |
| ATOM | 184 | C | LYS | A | 25 | −13.628 | 19.512 | −18.830 | 1.00 | 27.00 | C |
| ATOM | 185 | O | LYS | A | 25 | −12.599 | 19.208 | −18.225 | 1.00 | 27.27 | O |
| ATOM | 186 | N | LEU | A | 26 | −14.716 | 18.746 | −18.851 | 1.00 | 26.60 | N |
| ATOM | 187 | CA | LEU | A | 26 | −14.755 | 17.414 | −18.258 | 1.00 | 26.61 | C |
| ATOM | 188 | CB | LEU | A | 26 | −16.086 | 17.177 | −17.557 | 1.00 | 27.03 | C |
| ATOM | 189 | CG | LEU | A | 26 | −16.335 | 17.938 | −16.264 | 1.00 | 26.27 | C |
| ATOM | 190 | CD1 | LEU | A | 26 | −17.671 | 17.522 | −15.693 | 1.00 | 28.25 | C |
| ATOM | 191 | CD2 | LEU | A | 26 | −15.219 | 17.659 | −15.279 | 1.00 | 26.42 | C |
| ATOM | 192 | C | LEU | A | 26 | −14.609 | 16.371 | −19.356 | 1.00 | 27.70 | C |
| ATOM | 193 | O | LEU | A | 26 | −15.472 | 16.260 | −20.225 | 1.00 | 25.78 | O |
| ATOM | 194 | N | ASP | A | 27 | −13.528 | 15.600 | −19.320 | 1.00 | 27.94 | N |
| ATOM | 195 | CA | ASP | A | 27 | −13.326 | 14.547 | −20.311 | 1.00 | 29.39 | C |
| ATOM | 196 | CB | ASP | A | 27 | −11.876 | 14.078 | −20.311 | 1.00 | 29.51 | C |
| ATOM | 197 | CG | ASP | A | 27 | −10.896 | 15.220 | −20.414 | 1.00 | 32.09 | C |
| ATOM | 198 | OD1 | ASP | A | 27 | −10.258 | 15.543 | −19.391 | 1.00 | 35.91 | O |
| ATOM | 199 | OD2 | ASP | A | 27 | −10.691 | 15.848 | −21.473 | 1.00 | 33.14 | O |
| ATOM | 200 | C | ASP | A | 27 | −14.230 | 13.349 | −20.047 | 1.00 | 29.05 | C |
| ATOM | 201 | O | ASP | A | 27 | −14.413 | 12.494 | −20.911 | 1.00 | 29.61 | O |
| ATOM | 202 | N | GLY | A | 28 | −14.776 | 13.280 | −18.841 | 1.00 | 28.57 | N |
| ATOM | 203 | CA | GLY | A | 28 | −15.651 | 12.190 | −18.464 | 1.00 | 27.56 | C |
| ATOM | 204 | C | GLY | A | 28 | −16.364 | 12.574 | −17.191 | 1.00 | 26.55 | C |
| ATOM | 205 | O | GLY | A | 28 | −15.755 | 13.122 | −16.275 | 1.00 | 23.93 | O |
| ATOM | 206 | N | GLY | A | 29 | −17.660 | 12.305 | −17.135 | 1.00 | 25.37 | N |
| ATOM | 207 | CA | GLY | A | 29 | −18.428 | 12.641 | −15.957 | 1.00 | 25.02 | C |
| ATOM | 208 | C | GLY | A | 29 | −19.185 | 13.938 | −16.131 | 1.00 | 25.35 | C |
| ATOM | 209 | O | GLY | A | 29 | −19.288 | 14.474 | −17.234 | 1.00 | 25.34 | O |
| ATOM | 210 | N | ARG | A | 30 | −19.701 | 14.456 | −15.025 | 1.00 | 25.60 | N |
| ATOM | 211 | CA | ARG | A | 30 | −20.533 | 15.641 | −15.077 | 1.00 | 25.78 | C |
| ATOM | 212 | CB | ARG | A | 30 | −21.987 | 15.222 | −15.230 | 1.00 | 26.40 | C |
| ATOM | 213 | CG | ARG | A | 30 | −22.361 | 14.045 | −14.347 | 1.00 | 27.00 | C |

APPENDIX 1-continued

| | | | | | | | | | | | |
|---|---|---|---|---|---|---|---|---|---|---|---|
| ATOM | 214 | CD | ARG | A | 30 | −23.710 | 13.439 | −14.668 | 1.00 | 29.51 | C |
| ATOM | 215 | NE | ARG | A | 30 | −24.226 | 12.629 | −13.569 | 1.00 | 31.41 | N |
| ATOM | 216 | CZ | ARG | A | 30 | −25.378 | 11.975 | −13.612 | 1.00 | 35.18 | C |
| ATOM | 217 | NH1 | ARG | A | 30 | −26.131 | 12.031 | −14.701 | 1.00 | 33.60 | N |
| ATOM | 218 | NH2 | ARG | A | 30 | −25.780 | 11.262 | −12.568 | 1.00 | 38.37 | N |
| ATOM | 219 | C | ARG | A | 30 | −20.373 | 16.501 | −13.837 | 1.00 | 25.75 | C |
| ATOM | 220 | O | ARG | A | 30 | −19.950 | 16.028 | −12.784 | 1.00 | 26.61 | O |
| ATOM | 221 | N | TRP | A | 31 | −20.733 | 17.770 | −13.974 | 1.00 | 25.57 | N |
| ATOM | 222 | CA | TRP | A | 31 | −20.600 | 18.723 | −12.888 | 1.00 | 25.47 | C |
| ATOM | 223 | CB | TRP | A | 31 | −20.372 | 20.124 | −13.457 | 1.00 | 26.48 | C |
| ATOM | 224 | CG | TRP | A | 31 | −19.021 | 20.405 | −14.085 | 1.00 | 28.18 | C |
| ATOM | 225 | CD1 | TRP | A | 31 | −18.783 | 20.751 | −15.387 | 1.00 | 30.00 | C |
| ATOM | 226 | NE1 | TRP | A | 31 | −17.441 | 20.968 | −15.585 | 1.00 | 29.50 | N |
| ATOM | 227 | CE2 | TRP | A | 31 | −16.779 | 20.778 | −14.400 | 1.00 | 28.44 | C |
| ATOM | 228 | CD2 | TRP | A | 31 | −17.744 | 20.430 | −13.430 | 1.00 | 27.86 | C |
| ATOM | 229 | CE3 | TRP | A | 31 | −17.313 | 20.183 | −12.122 | 1.00 | 24.54 | C |
| ATOM | 230 | CZ3 | TRP | A | 31 | −15.962 | 20.288 | −11.832 | 1.00 | 27.39 | C |
| ATOM | 231 | CH2 | TRP | A | 31 | −15.033 | 20.632 | −12.818 | 1.00 | 26.51 | C |
| ATOM | 232 | CZ2 | TRP | A | 31 | −15.420 | 20.882 | −14.104 | 1.00 | 27.46 | C |
| ATOM | 233 | C | TRP | A | 31 | −21.826 | 18.768 | −11.977 | 1.00 | 25.20 | C |
| ATOM | 234 | O | TRP | A | 31 | −22.926 | 19.107 | −12.416 | 1.00 | 23.68 | O |
| ATOM | 235 | N | ARG | A | 32 | −21.629 | 18.436 | −10.705 | 1.00 | 24.37 | N |
| ATOM | 236 | CA | ARG | A | 32 | −22.691 | 18.535 | −9.715 | 1.00 | 25.26 | C |
| ATOM | 237 | CB | ARG | A | 32 | −22.331 | 17.719 | −8.483 | 1.00 | 24.30 | C |
| ATOM | 238 | CG | ARG | A | 32 | −23.541 | 17.197 | −7.755 | 1.00 | 27.11 | C |
| ATOM | 239 | CD | ARG | A | 32 | −23.262 | 16.712 | −6.352 | 1.00 | 27.60 | C |
| ATOM | 240 | NE | ARG | A | 32 | −23.046 | 15.271 | −6.310 | 1.00 | 29.99 | N |
| ATOM | 241 | CZ | ARG | A | 32 | −22.676 | 14.606 | −5.228 | 1.00 | 31.20 | C |
| ATOM | 242 | NH1 | ARG | A | 32 | −22.472 | 15.249 | −4.086 | 1.00 | 31.03 | N |
| ATOM | 243 | NH2 | ARG | A | 32 | −22.507 | 13.293 | −5.286 | 1.00 | 30.59 | N |
| ATOM | 244 | C | ARG | A | 32 | −22.767 | 19.996 | −9.322 | 1.00 | 25.50 | C |
| ATOM | 245 | O | ARG | A | 32 | −23.833 | 20.608 | −9.254 | 1.00 | 26.02 | O |
| ATOM | 246 | N | THR | A | 33 | −21.590 | 20.528 | −9.044 | 1.00 | 25.85 | N |
| ATOM | 247 | CA | THR | A | 33 | −21.410 | 21.909 | −8.693 | 1.00 | 26.91 | C |
| ATOM | 248 | CB | THR | A | 33 | −21.010 | 22.026 | −7.227 | 1.00 | 27.14 | C |
| ATOM | 249 | OG1 | THR | A | 33 | −22.098 | 21.590 | −6.405 | 1.00 | 27.25 | O |
| ATOM | 250 | CG2 | THR | A | 33 | −20.837 | 23.482 | −6.839 | 1.00 | 27.63 | C |
| ATOM | 251 | C | THR | A | 33 | −20.280 | 22.280 | −9.609 | 1.00 | 27.22 | C |
| ATOM | 252 | O | THR | A | 33 | −19.229 | 21.639 | −9.600 | 1.00 | 27.63 | O |
| ATOM | 253 | N | SER | A | 34 | −20.500 | 23.284 | −10.440 | 1.00 | 26.82 | N |
| ATOM | 254 | CA | SER | A | 34 | −19.513 | 23.600 | −11.451 | 1.00 | 26.90 | C |
| ATOM | 255 | CB | SER | A | 34 | −20.188 | 23.840 | −12.805 | 1.00 | 27.43 | C |
| ATOM | 256 | OG | SER | A | 34 | −21.241 | 24.778 | −12.697 | 1.00 | 25.73 | O |
| ATOM | 257 | C | SER | A | 34 | −18.634 | 24.763 | −11.036 | 1.00 | 25.93 | C |
| ATOM | 258 | O | SER | A | 34 | −19.037 | 25.610 | −10.239 | 1.00 | 26.76 | O |
| ATOM | 259 | N | PRO | A | 35 | −17.424 | 24.790 | −11.580 | 1.00 | 25.45 | N |
| ATOM | 260 | CA | PRO | A | 35 | −16.427 | 25.802 | −11.224 | 1.00 | 25.90 | C |
| ATOM | 261 | CB | PRO | A | 35 | −15.254 | 25.476 | −12.155 | 1.00 | 26.95 | C |
| ATOM | 262 | CG | PRO | A | 35 | −15.448 | 24.054 | −12.534 | 1.00 | 27.75 | C |
| ATOM | 263 | CD | PRO | A | 35 | −16.925 | 23.843 | −12.592 | 1.00 | 24.77 | C |
| ATOM | 264 | C | PRO | A | 35 | −16.894 | 27.234 | −11.467 | 1.00 | 26.85 | C |
| ATOM | 265 | O | PRO | A | 35 | −17.629 | 27.492 | −12.418 | 1.00 | 25.11 | O |
| ATOM | 266 | N | THR | A | 36 | −16.477 | 28.151 | −10.600 | 1.00 | 26.00 | N |
| ATOM | 267 | CA | THR | A | 36 | −16.782 | 29.565 | −10.777 | 1.00 | 26.13 | C |
| ATOM | 268 | CB | THR | A | 36 | −17.804 | 30.053 | −9.739 | 1.00 | 27.21 | C |
| ATOM | 269 | OG1 | THR | A | 36 | −17.134 | 30.298 | −8.497 | 1.00 | 28.02 | O |
| ATOM | 270 | CG2 | THR | A | 36 | −18.807 | 28.968 | −9.399 | 1.00 | 30.13 | C |
| ATOM | 271 | C | THR | A | 36 | −15.513 | 30.372 | −10.587 | 1.00 | 25.16 | C |
| ATOM | 272 | O | THR | A | 36 | −14.453 | 29.819 | −10.288 | 1.00 | 25.06 | O |
| ATOM | 273 | N | ASN | A | 37 | −15.623 | 31.684 | −10.763 | 1.00 | 23.04 | N |
| ATOM | 274 | CA | ASN | A | 37 | −14.509 | 32.563 | −10.472 | 1.00 | 23.51 | C |
| ATOM | 275 | CB | ASN | A | 37 | −14.892 | 34.029 | −10.673 | 1.00 | 22.69 | C |
| ATOM | 276 | CG | ASN | A | 37 | −15.122 | 34.389 | −12.119 | 1.00 | 23.93 | C |
| ATOM | 277 | OD1 | ASN | A | 37 | −14.460 | 33.870 | −13.014 | 1.00 | 21.38 | O |
| ATOM | 278 | ND2 | ASN | A | 37 | −16.060 | 35.298 | −12.356 | 1.00 | 22.90 | N |
| ATOM | 279 | C | ASN | A | 37 | −14.241 | 32.381 | −9.001 | 1.00 | 22.99 | C |
| ATOM | 280 | O | ASN | A | 37 | −15.136 | 31.998 | −8.250 | 1.00 | 21.76 | O |
| ATOM | 281 | N | VAL | A | 38 | −13.019 | 32.632 | −8.566 | 1.00 | 21.81 | N |
| ATOM | 282 | CA | VAL | A | 38 | −12.807 | 32.648 | −7.132 | 1.00 | 23.03 | C |
| ATOM | 283 | CB | VAL | A | 38 | −12.122 | 31.358 | −6.649 | 1.00 | 23.82 | C |
| ATOM | 284 | CG1 | VAL | A | 38 | −11.799 | 31.449 | −5.165 | 1.00 | 26.55 | C |
| ATOM | 285 | CG2 | VAL | A | 38 | −12.998 | 30.149 | −6.937 | 1.00 | 22.08 | C |
| ATOM | 286 | C | VAL | A | 38 | −11.971 | 33.841 | −6.731 | 1.00 | 22.62 | C |
| ATOM | 287 | O | VAL | A | 38 | −10.937 | 34.150 | −7.330 | 1.00 | 22.28 | O |
| ATOM | 288 | N | ALA | A | 39 | −12.481 | 34.529 | −5.721 | 1.00 | 22.00 | N |
| ATOM | 289 | CA | ALA | A | 39 | −11.898 | 35.752 | −5.210 | 1.00 | 24.24 | C |
| ATOM | 290 | CB | ALA | A | 39 | −12.883 | 36.412 | −4.259 | 1.00 | 23.20 | C |
| ATOM | 291 | C | ALA | A | 39 | −10.584 | 35.515 | −4.494 | 1.00 | 25.00 | C |
| ATOM | 292 | O | ALA | A | 39 | −10.342 | 34.433 | −3.958 | 1.00 | 24.33 | O |
| ATOM | 293 | N | ASN | A | 40 | −9.735 | 36.536 | −4.484 | 1.00 | 25.96 | N |

APPENDIX 1-continued

| | | | | | | | | | | | |
|---|---|---|---|---|---|---|---|---|---|---|---|
| ATOM | 294 | CA | ASN | A | 40 | −8.518 | 36.461 | −3.698 | 1.00 | 26.45 | C |
| ATOM | 295 | CB | ASN | A | 40 | −7.735 | 37.771 | −3.746 | 1.00 | 25.97 | C |
| ATOM | 296 | CG | ASN | A | 40 | −6.373 | 37.650 | −3.090 | 1.00 | 28.17 | C |
| ATOM | 297 | OD1 | ASN | A | 40 | −5.633 | 36.612 | −3.461 | 1.00 | 25.91 | O |
| ATOM | 298 | ND2 | ASN | A | 40 | −5.995 | 38.469 | −2.252 | 1.00 | 26.68 | N |
| ATOM | 299 | C | ASN | A | 40 | −8.885 | 36.128 | −2.256 | 1.00 | 26.05 | C |
| ATOM | 300 | O | ASN | A | 40 | −9.948 | 36.524 | −1.767 | 1.00 | 23.60 | O |
| ATOM | 301 | N | ASP | A | 41 | −7.998 | 35.392 | −1.594 | 1.00 | 25.12 | N |
| ATOM | 302 | CA | ASP | A | 41 | −8.187 | 34.949 | −0.212 | 1.00 | 23.72 | C |
| ATOM | 303 | CB | ASP | A | 41 | −8.005 | 36.100 | 0.774 | 1.00 | 23.36 | C |
| ATOM | 304 | CG | ASP | A | 41 | −6.611 | 36.672 | 0.740 | 1.00 | 28.68 | C |
| ATOM | 305 | OD1 | ASP | A | 41 | −5.650 | 35.892 | 0.570 | 1.00 | 24.35 | O |
| ATOM | 306 | OD2 | ASP | A | 41 | −6.381 | 37.891 | 0.867 | 1.00 | 26.98 | O |
| ATOM | 307 | C | ASP | A | 41 | −9.530 | 34.280 | 0.013 | 1.00 | 22.57 | C |
| ATOM | 308 | O | ASP | A | 41 | −10.162 | 34.462 | 1.052 | 1.00 | 22.71 | O |
| ATOM | 309 | N | GLN | A | 42 | −9.955 | 33.496 | −0.966 | 1.00 | 22.25 | N |
| ATOM | 310 | CA | GLN | A | 42 | −11.215 | 32.786 | −0.870 | 1.00 | 22.19 | C |
| ATOM | 311 | CB | GLN | A | 42 | −12.280 | 33.467 | −1.747 | 1.00 | 21.73 | C |
| ATOM | 312 | CG | GLN | A | 42 | −13.520 | 32.623 | −2.055 | 1.00 | 21.24 | C |
| ATOM | 313 | CD | GLN | A | 42 | −14.591 | 33.384 | −2.833 | 1.00 | 23.32 | C |
| ATOM | 314 | OE1 | GLN | A | 42 | −14.665 | 33.287 | −4.060 | 1.00 | 23.60 | O |
| ATOM | 315 | NE2 | GLN | A | 42 | −15.429 | 34.128 | −2.118 | 1.00 | 17.55 | N |
| ATOM | 316 | C | GLN | A | 42 | −11.021 | 31.332 | −1.274 | 1.00 | 21.63 | C |
| ATOM | 317 | O | GLN | A | 42 | −10.134 | 31.006 | −2.067 | 1.00 | 19.50 | O |
| ATOM | 318 | N | ILE | A | 43 | −11.834 | 30.462 | −0.685 | 1.00 | 22.96 | N |
| ATOM | 319 | CA | ILE | A | 43 | −11.865 | 29.054 | −1.045 | 1.00 | 24.37 | C |
| ATOM | 320 | CB | ILE | A | 43 | −11.506 | 28.158 | 0.154 | 1.00 | 26.25 | C |
| ATOM | 321 | CG1 | ILE | A | 43 | −10.135 | 28.514 | 0.721 | 1.00 | 28.14 | C |
| ATOM | 322 | CD1 | ILE | A | 43 | −9.863 | 27.871 | 2.063 | 1.00 | 31.84 | C |
| ATOM | 323 | CG2 | ILE | A | 43 | −11.549 | 26.688 | −0.249 | 1.00 | 25.52 | C |
| ATOM | 324 | C | ILE | A | 43 | −13.275 | 28.704 | −1.497 | 1.00 | 24.15 | C |
| ATOM | 325 | O | ILE | A | 43 | −14.253 | 29.072 | −0.845 | 1.00 | 22.87 | O |
| ATOM | 326 | N | LYS | A | 44 | −13.374 | 28.010 | −2.623 | 1.00 | 22.89 | N |
| ATOM | 327 | CA | LYS | A | 44 | −14.653 | 27.515 | −3.103 | 1.00 | 24.30 | C |
| ATOM | 328 | CB | LYS | A | 44 | −15.131 | 28.248 | −4.360 | 1.00 | 24.88 | C |
| ATOM | 329 | CG | LYS | A | 44 | −15.702 | 29.623 | −4.069 | 1.00 | 25.52 | C |
| ATOM | 330 | CD | LYS | A | 44 | −17.043 | 29.857 | −4.754 | 1.00 | 29.82 | C |
| ATOM | 331 | CE | LYS | A | 44 | −16.905 | 30.758 | −5.962 | 1.00 | 34.24 | C |
| ATOM | 332 | NZ | LYS | A | 44 | −18.014 | 31.749 | −6.025 | 1.00 | 41.35 | N |
| ATOM | 333 | C | LYS | A | 44 | −14.508 | 26.035 | −3.375 | 1.00 | 24.64 | C |
| ATOM | 334 | O | LYS | A | 44 | −13.402 | 25.530 | −3.574 | 1.00 | 24.26 | O |
| ATOM | 335 | N | THR | A | 45 | −15.634 | 25.343 | −3.378 | 1.00 | 23.64 | N |
| ATOM | 336 | CA | THR | A | 45 | −15.638 | 23.912 | −3.571 | 1.00 | 23.75 | C |
| ATOM | 337 | CB | THR | A | 45 | −16.227 | 23.227 | −2.329 | 1.00 | 24.63 | C |
| ATOM | 338 | OG1 | THR | A | 45 | −15.438 | 23.564 | −1.180 | 1.00 | 25.23 | O |
| ATOM | 339 | CG2 | THR | A | 45 | −16.088 | 21.716 | −2.425 | 1.00 | 22.69 | C |
| ATOM | 340 | C | THR | A | 45 | −16.479 | 23.607 | −4.788 | 1.00 | 24.16 | C |
| ATOM | 341 | O | THR | A | 45 | −17.595 | 24.101 | −4.921 | 1.00 | 23.69 | O |
| ATOM | 342 | N | PHE | A | 46 | −15.929 | 22.814 | −5.693 | 1.00 | 24.62 | N |
| ATOM | 343 | CA | PHE | A | 46 | −16.668 | 22.410 | −6.872 | 1.00 | 24.00 | C |
| ATOM | 344 | CB | PHE | A | 46 | −15.966 | 22.917 | −8.126 | 1.00 | 24.93 | C |
| ATOM | 345 | CG | PHE | A | 46 | −15.660 | 24.389 | −8.092 | 1.00 | 26.04 | C |
| ATOM | 346 | CD1 | PHE | A | 46 | −14.380 | 24.850 | −8.350 | 1.00 | 29.54 | C |
| ATOM | 347 | CE1 | PHE | A | 46 | −14.095 | 26.201 | −8.320 | 1.00 | 26.62 | C |
| ATOM | 348 | CZ | PHE | A | 46 | −15.092 | 27.110 | −8.028 | 1.00 | 26.20 | C |
| ATOM | 349 | CE2 | PHE | A | 46 | −16.373 | 26.666 | −7.766 | 1.00 | 26.71 | C |
| ATOM | 350 | CD2 | PHE | A | 46 | −16.652 | 25.312 | −7.798 | 1.00 | 24.99 | C |
| ATOM | 351 | C | PHE | A | 46 | −16.733 | 20.896 | −6.842 | 1.00 | 23.71 | C |
| ATOM | 352 | O | PHE | A | 46 | −15.910 | 20.261 | −6.184 | 1.00 | 22.84 | O |
| ATOM | 353 | N | VAL | A | 47 | −17.712 | 20.306 | −7.519 | 1.00 | 23.04 | N |
| ATOM | 354 | CA | VAL | A | 47 | −17.822 | 18.848 | −7.505 | 1.00 | 24.28 | C |
| ATOM | 355 | CB | VAL | A | 47 | −18.847 | 18.349 | −6.466 | 1.00 | 25.54 | C |
| ATOM | 356 | CG1 | VAL | A | 47 | −18.621 | 16.869 | −6.193 | 1.00 | 24.52 | C |
| ATOM | 357 | CG2 | VAL | A | 47 | −18.770 | 19.151 | −5.179 | 1.00 | 22.94 | C |
| ATOM | 358 | C | VAL | A | 47 | −18.209 | 18.190 | −8.825 | 1.00 | 25.74 | C |
| ATOM | 359 | O | VAL | A | 47 | −19.154 | 18.610 | −9.492 | 1.00 | 24.05 | O |
| ATOM | 360 | N | ALA | A | 48 | −17.502 | 17.113 | −9.157 | 1.00 | 26.98 | N |
| ATOM | 361 | CA | ALA | A | 48 | −17.764 | 16.357 | −10.377 | 1.00 | 29.96 | C |
| ATOM | 362 | CB | ALA | A | 48 | −16.533 | 16.368 | −11.267 | 1.00 | 29.88 | C |
| ATOM | 363 | C | ALA | A | 48 | −18.223 | 14.916 | −10.106 | 1.00 | 30.80 | C |
| ATOM | 364 | O | ALA | A | 48 | −17.763 | 14.275 | −9.159 | 1.00 | 32.03 | O |
| ATOM | 365 | N | GLU | A | 49 | −19.118 | 14.415 | −10.958 | 1.00 | 30.76 | N |
| ATOM | 366 | CA | GLU | A | 49 | −19.688 | 13.070 | −10.827 | 1.00 | 32.41 | C |
| ATOM | 367 | CB | GLU | A | 49 | −21.208 | 13.165 | −10.674 | 1.00 | 32.52 | C |
| ATOM | 368 | CG | GLU | A | 49 | −21.685 | 13.750 | −9.361 | 1.00 | 33.36 | C |
| ATOM | 369 | CD | GLU | A | 49 | −23.135 | 14.190 | −9.422 | 1.00 | 35.31 | C |
| ATOM | 370 | OE1 | GLU | A | 49 | −23.631 | 14.468 | −10.535 | 1.00 | 39.64 | O |
| ATOM | 371 | OE2 | GLU | A | 49 | −23.778 | 14.262 | −8.356 | 1.00 | 30.65 | O |
| ATOM | 372 | C | GLU | A | 49 | −19.405 | 12.167 | −12.028 | 1.00 | 32.60 | C |
| ATOM | 373 | O | GLU | A | 49 | −19.627 | 12.566 | −13.169 | 1.00 | 31.95 | O |

APPENDIX 1-continued

| | | | | | | | | | | | |
|---|---|---|---|---|---|---|---|---|---|---|---|
| ATOM | 374 | N | SER | A | 50 | −18.921 | 10.953 | −11.775 | 1.00 | 32.73 | N |
| ATOM | 375 | CA | SER | A | 50 | −18.743 | 9.971 | −12.843 | 1.00 | 32.17 | C |
| ATOM | 376 | CB | SER | A | 50 | −17.820 | 8.837 | −12.391 | 1.00 | 32.15 | C |
| ATOM | 377 | OG | SER | A | 50 | −18.278 | 7.582 | −12.862 | 1.00 | 28.65 | O |
| ATOM | 378 | C | SER | A | 50 | −20.151 | 9.457 | −13.137 | 1.00 | 33.46 | C |
| ATOM | 379 | O | SER | A | 50 | −20.925 | 9.249 | −12.207 | 1.00 | 32.67 | O |
| ATOM | 380 | N | ASN | A | 51 | −20.500 | 9.270 | −14.409 | 1.00 | 34.65 | N |
| ATOM | 381 | CA | ASN | A | 51 | −21.875 | 8.906 | −14.756 | 1.00 | 36.67 | C |
| ATOM | 382 | CB | ASN | A | 51 | −22.574 | 10.121 | −15.376 | 1.00 | 38.31 | C |
| ATOM | 383 | CG | ASN | A | 51 | −22.016 | 10.479 | −16.745 | 1.00 | 43.96 | C |
| ATOM | 384 | OD1 | ASN | A | 51 | −21.146 | 9.788 | −17.271 | 1.00 | 48.46 | O |
| ATOM | 385 | ND2 | ASN | A | 51 | −22.519 | 11.562 | −17.327 | 1.00 | 48.63 | N |
| ATOM | 386 | C | ASN | A | 51 | −22.091 | 7.690 | −15.672 | 1.00 | 35.67 | C |
| ATOM | 387 | O | ASN | A | 51 | −23.168 | 7.545 | −16.257 | 1.00 | 36.15 | O |
| ATOM | 388 | N | GLY | A | 52 | −21.094 | 6.821 | −15.801 | 1.00 | 33.90 | N |
| ATOM | 389 | CA | GLY | A | 52 | −21.223 | 5.665 | −16.680 | 1.00 | 32.29 | C |
| ATOM | 390 | C | GLY | A | 52 | −20.558 | 4.367 | −16.241 | 1.00 | 30.58 | C |
| ATOM | 391 | O | GLY | A | 52 | −19.988 | 4.284 | −15.154 | 1.00 | 30.65 | O |
| ATOM | 392 | N | PHE | A | 53 | −20.626 | 3.355 | −17.108 | 1.00 | 28.54 | N |
| ATOM | 393 | CA | PHE | A | 53 | −20.078 | 2.019 | −16.836 | 1.00 | 26.49 | C |
| ATOM | 394 | CB | PHE | A | 53 | −20.776 | 0.981 | −17.717 | 1.00 | 26.00 | C |
| ATOM | 395 | CG | PHE | A | 53 | −20.607 | −0.444 | −17.249 | 1.00 | 24.59 | C |
| ATOM | 396 | CD1 | PHE | A | 53 | −20.689 | −0.766 | −15.904 | 1.00 | 23.57 | C |
| ATOM | 397 | CE1 | PHE | A | 53 | −20.554 | −2.077 | −15.478 | 1.00 | 21.50 | C |
| ATOM | 398 | CZ | PHE | A | 53 | −20.337 | −3.083 | −16.399 | 1.00 | 21.31 | C |
| ATOM | 399 | CE2 | PHE | A | 53 | −20.257 | −2.778 | −17.742 | 1.00 | 22.36 | C |
| ATOM | 400 | CD2 | PHE | A | 53 | −20.394 | −1.466 | −18.162 | 1.00 | 23.09 | C |
| ATOM | 401 | C | PHE | A | 53 | −18.585 | 1.927 | −17.104 | 1.00 | 25.97 | C |
| ATOM | 402 | O | PHE | A | 53 | −18.130 | 2.227 | −18.206 | 1.00 | 25.48 | O |
| ATOM | 403 | N | MET | A | 54 | −17.831 | 1.477 | −16.107 | 1.00 | 25.47 | N |
| ATOM | 404 | CA | MET | A | 54 | −16.384 | 1.339 | −16.242 | 1.00 | 25.06 | C |
| ATOM | 405 | CB | MET | A | 54 | −16.026 | 0.160 | −17.148 | 1.00 | 26.08 | C |
| ATOM | 406 | CG | MET | A | 54 | −16.471 | −1.196 | −16.649 | 1.00 | 27.87 | C |
| ATOM | 407 | SD | MET | A | 54 | −15.754 | −2.520 | −17.642 | 1.00 | 35.01 | S |
| ATOM | 408 | CE | MET | A | 54 | −15.698 | −1.744 | −19.257 | 1.00 | 35.63 | C |
| ATOM | 409 | C | MET | A | 54 | −15.714 | 2.590 | −16.797 | 1.00 | 24.23 | C |
| ATOM | 410 | O | MET | A | 54 | −14.777 | 2.493 | −17.585 | 1.00 | 24.08 | O |
| ATOM | 411 | N | THR | A | 55 | −16.223 | 3.759 | −16.435 | 1.00 | 23.87 | N |
| ATOM | 412 | CA | THR | A | 55 | −15.563 | 5.004 | −16.793 | 1.00 | 23.80 | C |
| ATOM | 413 | CB | THR | A | 55 | −16.381 | 5.876 | −17.761 | 1.00 | 24.73 | C |
| ATOM | 414 | OG1 | THR | A | 55 | −17.738 | 5.961 | −17.307 | 1.00 | 26.42 | O |
| ATOM | 415 | CG2 | THR | A | 55 | −16.481 | 5.246 | −19.138 | 1.00 | 25.56 | C |
| ATOM | 416 | C | THR | A | 55 | −15.439 | 5.751 | −15.501 | 1.00 | 23.22 | C |
| ATOM | 417 | O | THR | A | 55 | −15.879 | 5.280 | −14.454 | 1.00 | 22.19 | O |
| ATOM | 418 | N | GLY | A | 56 | −14.875 | 6.942 | −15.575 | 1.00 | 25.23 | N |
| ATOM | 419 | CA | GLY | A | 56 | −14.687 | 7.712 | −14.374 | 1.00 | 25.93 | C |
| ATOM | 420 | C | GLY | A | 56 | −14.827 | 9.188 | −14.613 | 1.00 | 27.72 | C |
| ATOM | 421 | O | GLY | A | 56 | −15.301 | 9.638 | −15.658 | 1.00 | 28.31 | O |
| ATOM | 422 | N | THR | A | 57 | −14.409 | 9.944 | −13.613 | 1.00 | 27.41 | N |
| ATOM | 423 | CA | THR | A | 57 | −14.454 | 11.382 | −13.687 | 1.00 | 28.12 | C |
| ATOM | 424 | CB | THR | A | 57 | −14.827 | 11.963 | −12.328 | 1.00 | 28.49 | C |
| ATOM | 425 | OG1 | THR | A | 57 | −16.192 | 11.658 | −12.027 | 1.00 | 28.54 | O |
| ATOM | 426 | CG2 | THR | A | 57 | −14.807 | 13.475 | −12.398 | 1.00 | 29.80 | C |
| ATOM | 427 | C | THR | A | 57 | −13.088 | 11.906 | −14.048 | 1.00 | 28.27 | C |
| ATOM | 428 | O | THR | A | 57 | −12.095 | 11.553 | −13.414 | 1.00 | 27.85 | O |
| ATOM | 429 | N | GLU | A | 58 | −13.028 | 12.776 | −15.043 | 1.00 | 26.04 | N |
| ATOM | 430 | CA | GLU | A | 58 | −11.747 | 13.345 | −15.402 | 1.00 | 25.04 | C |
| ATOM | 431 | CB | GLU | A | 58 | −10.986 | 12.369 | −16.287 | 1.00 | 24.49 | C |
| ATOM | 432 | CG | GLU | A | 58 | −9.744 | 12.957 | −16.919 | 1.00 | 26.73 | C |
| ATOM | 433 | CD | GLU | A | 58 | −9.131 | 12.007 | −17.917 | 1.00 | 32.10 | C |
| ATOM | 434 | OE1 | GLU | A | 58 | −9.867 | 11.134 | −18.423 | 1.00 | 31.45 | O |
| ATOM | 435 | OE2 | GLU | A | 58 | −7.920 | 12.129 | −18.189 | 1.00 | 34.10 | O |
| ATOM | 436 | C | GLU | A | 58 | −11.865 | 14.688 | −16.097 | 1.00 | 25.39 | C |
| ATOM | 437 | O | GLU | A | 58 | −12.619 | 14.836 | −17.056 | 1.00 | 23.42 | O |
| ATOM | 438 | N | GLY | A | 59 | −11.106 | 15.667 | −15.620 | 1.00 | 24.93 | N |
| ATOM | 439 | CA | GLY | A | 59 | −11.136 | 16.968 | −16.251 | 1.00 | 24.69 | C |
| ATOM | 440 | C | GLY | A | 59 | −10.050 | 17.954 | −15.882 | 1.00 | 24.92 | C |
| ATOM | 441 | O | GLY | A | 59 | −9.126 | 17.660 | −15.118 | 1.00 | 23.09 | O |
| ATOM | 442 | N | THR | A | 60 | −10.190 | 19.147 | −16.449 | 1.00 | 23.57 | N |
| ATOM | 443 | CA | THR | A | 60 | −9.256 | 20.236 | −16.240 | 1.00 | 24.21 | C |
| ATOM | 444 | CB | THR | A | 60 | −8.290 | 20.344 | −17.429 | 1.00 | 25.09 | C |
| ATOM | 445 | OG1 | THR | A | 60 | −7.624 | 19.092 | −17.630 | 1.00 | 24.87 | O |
| ATOM | 446 | CG2 | THR | A | 60 | −7.159 | 21.308 | −17.106 | 1.00 | 24.43 | C |
| ATOM | 447 | C | THR | A | 60 | −9.996 | 21.552 | −16.116 | 1.00 | 24.54 | C |
| ATOM | 448 | O | THR | A | 60 | −10.766 | 21.928 | −17.000 | 1.00 | 25.46 | O |
| ATOM | 449 | N | ILE | A | 61 | −9.762 | 22.251 | −15.014 | 1.00 | 23.54 | N |
| ATOM | 450 | CA | ILE | A | 61 | −10.325 | 23.577 | −14.837 | 1.00 | 23.91 | C |
| ATOM | 451 | CB | ILE | A | 61 | −10.726 | 23.817 | −13.383 | 1.00 | 24.15 | C |
| ATOM | 452 | CG1 | ILE | A | 61 | −11.749 | 22.785 | −12.917 | 1.00 | 23.08 | C |
| ATOM | 453 | CD1 | ILE | A | 61 | −12.049 | 22.881 | −11.439 | 1.00 | 18.53 | C |

APPENDIX 1-continued

| | | | | | | | | | | | |
|---|---|---|---|---|---|---|---|---|---|---|---|
| ATOM | 454 | CG2 | ILE | A | 61 | −11.274 | 25.226 | −13.222 | 1.00 | 23.66 | C |
| ATOM | 455 | C | ILE | A | 61 | −9.256 | 24.586 | −15.204 | 1.00 | 24.81 | C |
| ATOM | 456 | O | ILE | A | 61 | −8.129 | 24.506 | −14.715 | 1.00 | 25.35 | O |
| ATOM | 457 | N | TYR | A | 62 | −9.608 | 25.542 | −16.054 | 1.00 | 24.24 | N |
| ATOM | 458 | CA | TYR | A | 62 | −8.668 | 26.580 | −16.445 | 1.00 | 24.50 | C |
| ATOM | 459 | CB | TYR | A | 62 | −8.594 | 26.693 | −17.960 | 1.00 | 24.65 | C |
| ATOM | 460 | CG | TYR | A | 62 | −8.051 | 25.487 | −18.680 | 1.00 | 26.90 | C |
| ATOM | 461 | CD1 | TYR | A | 62 | −8.907 | 24.546 | −19.229 | 1.00 | 25.16 | C |
| ATOM | 462 | CE1 | TYR | A | 62 | −8.420 | 23.451 | −19.909 | 1.00 | 27.18 | C |
| ATOM | 463 | CZ | TYR | A | 62 | −7.060 | 23.290 | −20.054 | 1.00 | 26.12 | C |
| ATOM | 464 | OH | TYR | A | 62 | −6.573 | 22.197 | −20.731 | 1.00 | 26.72 | O |
| ATOM | 465 | CE2 | TYR | A | 62 | −6.186 | 24.216 | −19.523 | 1.00 | 24.12 | C |
| ATOM | 466 | CD2 | TYR | A | 62 | −6.684 | 25.309 | −18.844 | 1.00 | 25.80 | C |
| ATOM | 467 | C | TYR | A | 62 | −9.046 | 27.948 | −15.899 | 1.00 | 24.69 | C |
| ATOM | 468 | O | TYR | A | 62 | −10.178 | 28.406 | −16.068 | 1.00 | 25.15 | O |
| ATOM | 469 | N | TYR | A | 63 | −8.082 | 28.609 | −15.269 | 1.00 | 23.33 | N |
| ATOM | 470 | CA | TYR | A | 63 | −8.287 | 29.955 | −14.760 | 1.00 | 24.10 | C |
| ATOM | 471 | CB | TYR | A | 63 | −8.147 | 30.004 | −13.241 | 1.00 | 24.17 | C |
| ATOM | 472 | CG | TYR | A | 63 | −9.302 | 29.446 | −12.449 | 1.00 | 26.52 | C |
| ATOM | 473 | CD1 | TYR | A | 63 | −9.170 | 28.252 | −11.759 | 1.00 | 27.18 | C |
| ATOM | 474 | CE1 | TYR | A | 63 | −10.208 | 27.737 | −11.016 | 1.00 | 28.68 | C |
| ATOM | 475 | CZ | TYR | A | 63 | −11.400 | 28.422 | −10.947 | 1.00 | 24.41 | C |
| ATOM | 476 | OH | TYR | A | 63 | −12.436 | 27.906 | −10.205 | 1.00 | 18.74 | O |
| ATOM | 477 | CE2 | TYR | A | 63 | −11.558 | 29.619 | −11.614 | 1.00 | 25.27 | C |
| ATOM | 478 | CD2 | TYR | A | 63 | −10.509 | 30.128 | −12.356 | 1.00 | 27.38 | C |
| ATOM | 479 | C | TYR | A | 63 | −7.269 | 30.921 | −15.338 | 1.00 | 24.54 | C |
| ATOM | 480 | O | TYR | A | 63 | −6.135 | 30.551 | −15.649 | 1.00 | 23.25 | O |
| ATOM | 481 | N | SER | A | 64 | −7.690 | 32.174 | −15.434 | 1.00 | 25.09 | N |
| ATOM | 482 | CA | SER | A | 64 | −6.856 | 33.260 | −15.905 | 1.00 | 25.59 | C |
| ATOM | 483 | CB | SER | A | 64 | −7.612 | 34.025 | −16.994 | 1.00 | 24.67 | C |
| ATOM | 484 | OG | SER | A | 64 | −6.897 | 35.162 | −17.439 | 1.00 | 24.48 | O |
| ATOM | 485 | C | SER | A | 64 | −6.554 | 34.198 | −14.736 | 1.00 | 27.22 | C |
| ATOM | 486 | O | SER | A | 64 | −7.433 | 34.480 | −13.923 | 1.00 | 27.09 | O |
| ATOM | 487 | N | ILE | A | 65 | −5.309 | 34.651 | −14.627 | 1.00 | 29.47 | N |
| ATOM | 488 | CA | ILE | A | 65 | −4.967 | 35.674 | −13.646 | 1.00 | 33.07 | C |
| ATOM | 489 | CB | ILE | A | 65 | −3.669 | 35.308 | −12.873 | 1.00 | 32.14 | C |
| ATOM | 490 | CG1 | ILE | A | 65 | −3.859 | 33.978 | −12.131 | 1.00 | 32.81 | C |
| ATOM | 491 | CD1 | ILE | A | 65 | −2.592 | 33.411 | −11.519 | 1.00 | 32.19 | C |
| ATOM | 492 | CG2 | ILE | A | 65 | −3.294 | 36.399 | −11.879 | 1.00 | 35.96 | C |
| ATOM | 493 | C | ILE | A | 65 | −4.878 | 36.998 | −14.424 | 1.00 | 34.72 | C |
| ATOM | 494 | O | ILE | A | 65 | −3.849 | 37.310 | −15.024 | 1.00 | 34.58 | O |
| ATOM | 495 | N | ASN | A | 66 | −6.025 | 37.683 | −14.503 | 1.00 | 38.05 | N |
| ATOM | 496 | CA | ASN | A | 66 | −6.179 | 39.056 | −15.018 | 1.00 | 39.99 | C |
| ATOM | 497 | CB | ASN | A | 66 | −5.946 | 40.075 | −13.903 | 1.00 | 42.08 | C |
| ATOM | 498 | CG | ASN | A | 66 | −6.920 | 39.913 | −12.752 | 1.00 | 47.88 | C |
| ATOM | 499 | OD1 | ASN | A | 66 | −8.104 | 39.654 | −12.961 | 1.00 | 54.24 | O |
| ATOM | 500 | ND2 | ASN | A | 66 | −6.418 | 40.044 | −11.531 | 1.00 | 52.65 | N |
| ATOM | 501 | C | ASN | A | 66 | −5.246 | 39.498 | −16.147 | 1.00 | 39.26 | C |
| ATOM | 502 | O | ASN | A | 66 | −4.584 | 40.537 | −16.052 | 1.00 | 39.80 | O |
| ATOM | 503 | N | GLY | A | 67 | −5.190 | 38.689 | −17.201 | 1.00 | 38.73 | N |
| ATOM | 504 | CA | GLY | A | 67 | −4.446 | 39.023 | −18.405 | 1.00 | 37.19 | C |
| ATOM | 505 | C | GLY | A | 67 | −2.989 | 38.650 | −18.300 | 1.00 | 36.09 | C |
| ATOM | 506 | O | GLY | A | 67 | −2.225 | 38.720 | −19.265 | 1.00 | 37.58 | O |
| ATOM | 507 | N | GLU | A | 68 | −2.629 | 38.204 | −17.108 | 1.00 | 33.60 | N |
| ATOM | 508 | CA | GLU | A | 68 | −1.256 | 37.894 | −16.772 | 1.00 | 32.14 | C |
| ATOM | 509 | CB | GLU | A | 68 | −0.993 | 38.393 | −15.349 | 1.00 | 33.24 | C |
| ATOM | 510 | CG | GLU | A | 68 | 0.461 | 38.592 | −14.986 | 1.00 | 35.30 | C |
| ATOM | 511 | CD | GLU | A | 68 | 0.676 | 38.588 | −13.484 | 1.00 | 38.70 | C |
| ATOM | 512 | OE1 | GLU | A | 68 | −0.277 | 38.717 | −12.714 | 1.00 | 38.53 | O |
| ATOM | 513 | OE2 | GLU | A | 68 | 1.925 | 38.431 | −13.064 | 1.00 | 37.16 | N |
| ATOM | 514 | C | GLU | A | 68 | −0.821 | 36.424 | −16.892 | 1.00 | 29.98 | C |
| ATOM | 515 | O | GLU | A | 68 | 0.318 | 36.161 | −17.268 | 1.00 | 28.96 | O |
| ATOM | 516 | N | ALA | A | 69 | −1.690 | 35.467 | −16.570 | 1.00 | 26.86 | N |
| ATOM | 517 | CA | ALA | A | 69 | −1.254 | 34.066 | −16.583 | 1.00 | 25.20 | C |
| ATOM | 518 | CB | ALA | A | 69 | −0.341 | 33.795 | −15.389 | 1.00 | 24.76 | C |
| ATOM | 519 | C | ALA | A | 69 | −2.375 | 33.037 | −16.611 | 1.00 | 24.66 | C |
| ATOM | 520 | O | ALA | A | 69 | −3.491 | 33.302 | −16.170 | 1.00 | 23.50 | O |
| ATOM | 521 | N | GLU | A | 70 | −2.058 | 31.848 | −17.113 | 1.00 | 23.75 | N |
| ATOM | 522 | CA | GLU | A | 70 | −3.035 | 30.770 | −17.158 | 1.00 | 24.20 | C |
| ATOM | 523 | CB | GLU | A | 70 | −3.127 | 30.166 | −18.560 | 1.00 | 23.76 | C |
| ATOM | 524 | CG | GLU | A | 70 | −4.470 | 29.502 | −18.803 | 1.00 | 26.21 | C |
| ATOM | 525 | CD | GLU | A | 70 | −4.569 | 28.786 | −20.133 | 1.00 | 30.59 | C |
| ATOM | 526 | OE1 | GLU | A | 70 | −3.638 | 28.036 | −20.493 | 1.00 | 35.67 | O |
| ATOM | 527 | OE2 | GLU | A | 70 | −5.600 | 28.964 | −20.810 | 1.00 | 28.27 | O |
| ATOM | 528 | C | GLU | A | 70 | −2.739 | 29.673 | −16.135 | 1.00 | 24.75 | C |
| ATOM | 529 | O | GLU | A | 70 | −1.606 | 29.202 | −16.022 | 1.00 | 23.63 | O |
| ATOM | 530 | N | ILE | A | 71 | −3.765 | 29.281 | −15.385 | 1.00 | 23.84 | N |
| ATOM | 531 | CA | ILE | A | 71 | −3.649 | 28.179 | −14.436 | 1.00 | 25.53 | C |
| ATOM | 532 | CB | ILE | A | 71 | −4.204 | 28.578 | −13.054 | 1.00 | 24.67 | C |
| ATOM | 533 | CG1 | ILE | A | 71 | −3.591 | 29.893 | −12.571 | 1.00 | 28.07 | C |

APPENDIX 1-continued

| | | | | | | | | | | | |
|---|---|---|---|---|---|---|---|---|---|---|---|
| ATOM | 534 | CD1 | ILE | A | 71 | −2.113 | 29.808 | −12.278 | 1.00 | 29.93 | C |
| ATOM | 535 | CG2 | ILE | A | 71 | −3.965 | 27.460 | −12.047 | 1.00 | 25.65 | C |
| ATOM | 536 | C | ILE | A | 71 | −4.428 | 26.968 | −14.943 | 1.00 | 25.20 | C |
| ATOM | 537 | O | ILE | A | 71 | −5.555 | 27.108 | −15.418 | 1.00 | 24.13 | O |
| ATOM | 538 | N | SER | A | 72 | −3.831 | 25.783 | −14.842 | 1.00 | 23.65 | N |
| ATOM | 539 | CA | SER | A | 72 | −4.509 | 24.548 | −15.227 | 1.00 | 22.64 | C |
| ATOM | 540 | CB | SER | A | 72 | −3.801 | 23.869 | −16.400 | 1.00 | 22.07 | C |
| ATOM | 541 | OG | SER | A | 72 | −3.530 | 24.784 | −17.443 | 1.00 | 27.15 | O |
| ATOM | 542 | C | SER | A | 72 | −4.564 | 23.580 | −14.051 | 1.00 | 21.99 | C |
| ATOM | 543 | O | SER | A | 72 | −3.536 | 23.249 | −13.461 | 1.00 | 21.52 | O |
| ATOM | 544 | N | LEU | A | 73 | −5.768 | 23.128 | −13.717 | 1.00 | 22.03 | N |
| ATOM | 545 | CA | LEU | A | 73 | −5.956 | 22.188 | −12.620 | 1.00 | 21.77 | C |
| ATOM | 546 | CB | LEU | A | 73 | −6.813 | 22.808 | −11.513 | 1.00 | 21.46 | C |
| ATOM | 547 | CG | LEU | A | 73 | −6.474 | 24.245 | −11.090 | 1.00 | 22.77 | C |
| ATOM | 548 | CD1 | LEU | A | 73 | −7.560 | 24.812 | −10.183 | 1.00 | 23.15 | C |
| ATOM | 549 | CD2 | LEU | A | 73 | −5.102 | 24.346 | −10.424 | 1.00 | 16.28 | C |
| ATOM | 550 | C | LEU | A | 73 | −6.594 | 20.921 | −13.173 | 1.00 | 23.85 | C |
| ATOM | 551 | O | LEU | A | 73 | −7.752 | 20.921 | −13.593 | 1.00 | 22.12 | O |
| ATOM | 552 | N | TYR | A | 74 | −5.813 | 19.848 | −13.183 | 1.00 | 22.69 | N |
| ATOM | 553 | CA | TYR | A | 74 | −6.239 | 18.567 | −13.728 | 1.00 | 22.49 | C |
| ATOM | 554 | CB | TYR | A | 74 | −5.120 | 17.995 | −14.612 | 1.00 | 21.92 | C |
| ATOM | 555 | CG | TYR | A | 74 | −5.304 | 16.565 | −15.085 | 1.00 | 22.39 | C |
| ATOM | 556 | CD1 | TYR | A | 74 | −6.152 | 16.263 | −16.143 | 1.00 | 25.97 | C |
| ATOM | 557 | CE1 | TYR | A | 74 | −6.313 | 14.959 | −16.584 | 1.00 | 27.83 | C |
| ATOM | 558 | CZ | TYR | A | 74 | −5.614 | 13.940 | −15.971 | 1.00 | 29.25 | C |
| ATOM | 559 | OH | TYR | A | 74 | −5.773 | 12.644 | −16.410 | 1.00 | 25.74 | O |
| ATOM | 560 | CE2 | TYR | A | 74 | −4.759 | 14.214 | −14.924 | 1.00 | 25.79 | C |
| ATOM | 561 | CD2 | TYR | A | 74 | −4.603 | 15.520 | −14.491 | 1.00 | 23.40 | C |
| ATOM | 562 | C | TYR | A | 74 | −6.579 | 17.597 | −12.608 | 1.00 | 22.85 | C |
| ATOM | 563 | O | TYR | A | 74 | −5.907 | 17.562 | −11.578 | 1.00 | 21.60 | O |
| ATOM | 564 | N | PHE | A | 75 | −7.644 | 16.830 | −12.803 | 1.00 | 21.68 | N |
| ATOM | 565 | CA | PHE | A | 75 | −8.019 | 15.793 | −11.854 | 1.00 | 22.34 | C |
| ATOM | 566 | CB | PHE | A | 75 | −9.126 | 16.269 | −10.912 | 1.00 | 22.81 | C |
| ATOM | 567 | CG | PHE | A | 75 | −10.344 | 16.781 | −11.620 | 1.00 | 23.45 | C |
| ATOM | 568 | CD1 | PHE | A | 75 | −11.353 | 15.917 | −12.017 | 1.00 | 23.17 | C |
| ATOM | 569 | CE1 | PHE | A | 75 | −12.471 | 16.393 | −12.673 | 1.00 | 27.45 | C |
| ATOM | 570 | CZ | PHE | A | 75 | −12.590 | 17.743 | −12.936 | 1.00 | 22.60 | C |
| ATOM | 571 | CE2 | PHE | A | 75 | −11.592 | 18.611 | −12.547 | 1.00 | 23.01 | C |
| ATOM | 572 | CD2 | PHE | A | 75 | −10.479 | 18.130 | −11.893 | 1.00 | 23.73 | C |
| ATOM | 573 | C | PHE | A | 75 | −8.474 | 14.552 | −12.605 | 1.00 | 21.45 | C |
| ATOM | 574 | O | PHE | A | 75 | −9.048 | 14.644 | −13.691 | 1.00 | 20.44 | O |
| ATOM | 575 | N | ASP | A | 76 | −8.199 | 13.392 | −12.021 | 1.00 | 20.36 | N |
| ATOM | 576 | CA | ASP | A | 76 | −8.636 | 12.123 | −12.584 | 1.00 | 19.20 | C |
| ATOM | 577 | CB | ASP | A | 76 | −7.596 | 11.561 | −13.556 | 1.00 | 19.48 | C |
| ATOM | 578 | CG | ASP | A | 76 | −8.096 | 10.335 | −14.302 | 1.00 | 22.24 | C |
| ATOM | 579 | OD1 | ASP | A | 76 | −9.329 | 10.155 | −14.402 | 1.00 | 21.23 | O |
| ATOM | 580 | OD2 | ASP | A | 76 | −7.330 | 9.497 | −14.822 | 1.00 | 28.22 | O |
| ATOM | 581 | C | ASP | A | 76 | −8.921 | 11.125 | −11.467 | 1.00 | 18.15 | C |
| ATOM | 582 | O | ASP | A | 76 | −8.063 | 10.842 | −10.633 | 1.00 | 15.04 | O |
| ATOM | 583 | N | ASN | A | 77 | −10.149 | 10.622 | −11.450 | 1.00 | 16.70 | N |
| ATOM | 584 | CA | ASN | A | 77 | −10.593 | 9.616 | −10.501 | 1.00 | 17.65 | C |
| ATOM | 585 | CB | ASN | A | 77 | −11.787 | 10.155 | −9.703 | 1.00 | 16.46 | C |
| ATOM | 586 | CG | ASN | A | 77 | −12.111 | 9.327 | −8.463 | 1.00 | 20.79 | C |
| ATOM | 587 | OD1 | ASN | A | 77 | −11.996 | 8.102 | −8.463 | 1.00 | 15.07 | O |
| ATOM | 588 | ND2 | ASN | A | 77 | −12.539 | 10.005 | −7.401 | 1.00 | 18.53 | N |
| ATOM | 589 | C | ASN | A | 77 | −11.029 | 8.485 | −11.412 | 1.00 | 20.12 | C |
| ATOM | 590 | O | ASN | A | 77 | −12.203 | 8.401 | −11.771 | 1.00 | 20.56 | O |
| ATOM | 591 | N | PRO | A | 78 | −10.091 | 7.647 | −11.846 | 1.00 | 20.61 | N |
| ATOM | 592 | CA | PRO | A | 78 | −10.442 | 6.618 | −12.821 | 1.00 | 20.41 | C |
| ATOM | 593 | CB | PRO | A | 78 | −9.094 | 6.059 | −13.296 | 1.00 | 21.13 | C |
| ATOM | 594 | CG | PRO | A | 78 | −8.047 | 6.711 | −12.501 | 1.00 | 19.86 | C |
| ATOM | 595 | CD | PRO | A | 78 | −8.670 | 7.594 | −11.464 | 1.00 | 19.47 | C |
| ATOM | 596 | C | PRO | A | 78 | −11.260 | 5.500 | −12.252 | 1.00 | 22.03 | C |
| ATOM | 597 | O | PRO | A | 78 | −11.557 | 5.402 | −11.058 | 1.00 | 20.62 | O |
| ATOM | 598 | N | PHE | A | 79 | −11.601 | 4.623 | −13.174 | 1.00 | 22.52 | N |
| ATOM | 599 | CA | PHE | A | 79 | −12.444 | 3.504 | −12.890 | 1.00 | 23.95 | C |
| ATOM | 600 | CB | PHE | A | 79 | −12.727 | 2.777 | −14.177 | 1.00 | 23.84 | C |
| ATOM | 601 | CG | PHE | A | 79 | −13.351 | 1.491 | −13.946 | 1.00 | 22.20 | C |
| ATOM | 602 | CD1 | PHE | A | 79 | −14.346 | 1.399 | −13.001 | 1.00 | 21.49 | C |
| ATOM | 603 | CE1 | PHE | A | 79 | −14.930 | 0.216 | −12.725 | 1.00 | 21.53 | C |
| ATOM | 604 | CZ | PHE | A | 79 | −14.516 | −0.914 | −13.386 | 1.00 | 22.05 | C |
| ATOM | 605 | CE2 | PHE | A | 79 | −13.503 | −0.840 | −14.322 | 1.00 | 20.33 | C |
| ATOM | 606 | CD2 | PHE | A | 79 | −12.917 | 0.360 | −14.591 | 1.00 | 20.10 | C |
| ATOM | 607 | C | PHE | A | 79 | −11.774 | 2.564 | −11.900 | 1.00 | 25.71 | C |
| ATOM | 608 | O | PHE | A | 79 | −12.321 | 2.243 | −10.846 | 1.00 | 25.70 | O |
| ATOM | 609 | N | ALA | A | 80 | −10.602 | 2.084 | −12.275 | 1.00 | 26.68 | N |
| ATOM | 610 | CA | ALA | A | 80 | −9.767 | 1.353 | −11.353 | 1.00 | 28.43 | C |
| ATOM | 611 | CB | ALA | A | 80 | −9.698 | −0.099 | −11.710 | 1.00 | 28.35 | C |
| ATOM | 612 | C | ALA | A | 80 | −8.435 | 2.024 | −11.559 | 1.00 | 29.41 | C |
| ATOM | 613 | O | ALA | A | 80 | −8.074 | 2.364 | −12.685 | 1.00 | 30.73 | O |

APPENDIX 1-continued

| | | | | | | | | | | | |
|---|---|---|---|---|---|---|---|---|---|---|---|
| ATOM | 614 | N | GLY | A | 81 | −7.714 | 2.261 | −10.480 | 1.00 | 29.53 | N |
| ATOM | 615 | CA | GLY | A | 81 | −6.415 | 2.867 | −10.619 | 1.00 | 29.20 | C |
| ATOM | 616 | C | GLY | A | 81 | −6.176 | 3.856 | −9.520 | 1.00 | 29.47 | C |
| ATOM | 617 | O | GLY | A | 81 | −6.923 | 3.929 | −8.545 | 1.00 | 30.93 | O |
| ATOM | 618 | N | SER | A | 82 | −5.102 | 4.607 | −9.659 | 1.00 | 27.97 | N |
| ATOM | 619 | CA | SER | A | 82 | −4.851 | 5.640 | −8.700 | 1.00 | 26.30 | C |
| ATOM | 620 | CB | SER | A | 82 | −3.355 | 5.795 | −8.445 | 1.00 | 26.99 | C |
| ATOM | 621 | OG | SER | A | 82 | −2.784 | 4.554 | −8.071 | 1.00 | 30.52 | O |
| ATOM | 622 | C | SER | A | 82 | −5.423 | 6.903 | −9.293 | 1.00 | 24.01 | C |
| ATOM | 623 | O | SER | A | 82 | −5.406 | 7.102 | −10.511 | 1.00 | 21.96 | O |
| ATOM | 624 | N | ASN | A | 83 | −5.986 | 7.725 | −8.424 | 1.00 | 22.72 | N |
| ATOM | 625 | CA | ASN | A | 83 | −6.409 | 9.051 | −8.802 | 1.00 | 23.89 | C |
| ATOM | 626 | CB | ASN | A | 83 | −7.070 | 9.724 | −7.601 | 1.00 | 23.53 | C |
| ATOM | 627 | CG | ASN | A | 83 | −8.403 | 9.093 | −7.235 | 1.00 | 28.45 | C |
| ATOM | 628 | OD1 | ASN | A | 83 | −9.183 | 8.720 | −8.107 | 1.00 | 29.35 | O |
| ATOM | 629 | ND2 | ASN | A | 83 | −8.674 | 8.982 | −5.939 | 1.00 | 31.22 | N |
| ATOM | 630 | C | ASN | A | 83 | −5.162 | 9.830 | −9.232 | 1.00 | 23.74 | C |
| ATOM | 631 | O | ASN | A | 83 | −4.062 | 9.564 | −8.744 | 1.00 | 23.77 | O |
| ATOM | 632 | N | LYS | A | 84 | −5.323 | 10.767 | −10.161 | 1.00 | 23.79 | N |
| ATOM | 633 | CA | LYS | A | 84 | −4.209 | 11.591 | −10.626 | 1.00 | 24.20 | C |
| ATOM | 634 | CB | LYS | A | 84 | −3.842 | 11.264 | −12.079 | 1.00 | 25.35 | C |
| ATOM | 635 | CG | LYS | A | 84 | −3.097 | 9.958 | −12.270 | 1.00 | 28.77 | C |
| ATOM | 636 | CD | LYS | A | 84 | −2.470 | 9.851 | −13.661 | 1.00 | 36.11 | C |
| ATOM | 637 | CE | LYS | A | 84 | −3.485 | 9.429 | −14.707 | 1.00 | 40.41 | C |
| ATOM | 638 | NZ | LYS | A | 84 | −2.918 | 8.424 | −15.653 | 1.00 | 44.23 | N |
| ATOM | 639 | C | LYS | A | 84 | −4.603 | 13.051 | −10.537 | 1.00 | 23.62 | C |
| ATOM | 640 | O | LYS | A | 84 | −5.752 | 13.403 | −10.793 | 1.00 | 21.79 | O |
| ATOM | 641 | N | TYR | A | 85 | −3.657 | 13.905 | −10.168 | 1.00 | 22.99 | N |
| ATOM | 642 | CA | TYR | A | 85 | −3.936 | 15.331 | −10.108 | 1.00 | 23.66 | C |
| ATOM | 643 | CB | TYR | A | 85 | −4.434 | 15.748 | −8.718 | 1.00 | 22.81 | C |
| ATOM | 644 | CG | TYR | A | 85 | −5.471 | 14.872 | −8.029 | 1.00 | 25.71 | C |
| ATOM | 645 | CD1 | TYR | A | 85 | −5.091 | 13.773 | −7.266 | 1.00 | 28.50 | C |
| ATOM | 646 | CE1 | TYR | A | 85 | −6.032 | 12.994 | −6.607 | 1.00 | 28.72 | C |
| ATOM | 647 | CZ | TYR | A | 85 | −7.370 | 13.323 | −6.691 | 1.00 | 27.90 | C |
| ATOM | 648 | OH | TYR | A | 85 | −8.314 | 12.558 | −6.041 | 1.00 | 26.65 | O |
| ATOM | 649 | CE2 | TYR | A | 85 | −7.770 | 14.417 | −7.426 | 1.00 | 26.22 | C |
| ATOM | 650 | CD2 | TYR | A | 85 | −6.824 | 15.190 | −8.082 | 1.00 | 24.50 | C |
| ATOM | 651 | C | TYR | A | 85 | −2.690 | 16.155 | −10.433 | 1.00 | 24.09 | C |
| ATOM | 652 | O | TYR | A | 85 | −1.567 | 15.734 | −10.151 | 1.00 | 21.65 | O |
| ATOM | 653 | N | ASP | A | 86 | −2.897 | 17.324 | −11.034 | 1.00 | 23.43 | N |
| ATOM | 654 | CA | ASP | A | 86 | −1.814 | 18.283 | −11.254 | 1.00 | 24.93 | C |
| ATOM | 655 | CB | ASP | A | 86 | −0.979 | 17.961 | −12.495 | 1.00 | 24.97 | C |
| ATOM | 656 | CG | ASP | A | 86 | 0.474 | 18.390 | −12.341 | 1.00 | 27.97 | C |
| ATOM | 657 | OD1 | ASP | A | 86 | 0.861 | 18.775 | −11.216 | 1.00 | 26.47 | O |
| ATOM | 658 | OD2 | ASP | A | 86 | 1.303 | 18.367 | −13.275 | 1.00 | 30.47 | O |
| ATOM | 659 | C | ASP | A | 86 | −2.340 | 19.708 | −11.350 | 1.00 | 24.39 | C |
| ATOM | 660 | O | ASP | A | 86 | −3.472 | 19.944 | −11.773 | 1.00 | 25.08 | O |
| ATOM | 661 | N | GLY | A | 87 | −1.503 | 20.650 | −10.935 | 1.00 | 25.42 | N |
| ATOM | 662 | CA | GLY | A | 87 | −1.804 | 22.061 | −11.036 | 1.00 | 26.07 | C |
| ATOM | 663 | C | GLY | A | 87 | −0.607 | 22.726 | −11.686 | 1.00 | 27.17 | C |
| ATOM | 664 | O | GLY | A | 87 | 0.523 | 22.534 | −11.239 | 1.00 | 25.48 | O |
| ATOM | 665 | N | HIS | A | 88 | −0.837 | 23.498 | −12.742 | 1.00 | 26.94 | N |
| ATOM | 666 | CA | HIS | A | 88 | 0.274 | 24.131 | −13.447 | 1.00 | 27.76 | C |
| ATOM | 667 | CB | HIS | A | 88 | 0.659 | 23.299 | −14.674 | 1.00 | 27.46 | C |
| ATOM | 668 | CG | HIS | A | 88 | 1.617 | 23.981 | −15.603 | 1.00 | 30.53 | C |
| ATOM | 669 | ND1 | HIS | A | 88 | 2.974 | 23.739 | −15.583 | 1.00 | 30.43 | N |
| ATOM | 670 | CE1 | HIS | A | 88 | 3.563 | 24.465 | −16.517 | 1.00 | 29.34 | C |
| ATOM | 671 | NE2 | HIS | A | 88 | 2.636 | 25.166 | −17.145 | 1.00 | 30.58 | N |
| ATOM | 672 | CD2 | HIS | A | 88 | 1.410 | 24.878 | −16.596 | 1.00 | 30.46 | C |
| ATOM | 673 | C | HIS | A | 88 | 0.029 | 25.581 | −13.850 | 1.00 | 27.84 | C |
| ATOM | 674 | O | HIS | A | 88 | −1.069 | 25.955 | −14.267 | 1.00 | 26.38 | O |
| ATOM | 675 | N | SER | A | 89 | 1.077 | 26.386 | −13.719 | 1.00 | 26.97 | N |
| ATOM | 676 | CA | SER | A | 89 | 1.039 | 27.791 | −14.093 | 1.00 | 24.52 | C |
| ATOM | 677 | CB | SER | A | 89 | 1.502 | 28.665 | −12.932 | 1.00 | 25.63 | C |
| ATOM | 678 | OG | SER | A | 89 | 1.724 | 29.994 | −13.371 | 1.00 | 25.88 | O |
| ATOM | 679 | C | SER | A | 89 | 1.957 | 28.039 | −15.276 | 1.00 | 23.29 | C |
| ATOM | 680 | O | SER | A | 89 | 3.120 | 27.638 | −15.260 | 1.00 | 22.35 | O |
| ATOM | 681 | N | ASN | A | 90 | 1.449 | 28.721 | −16.295 | 1.00 | 21.58 | N |
| ATOM | 682 | CA | ASN | A | 90 | 2.274 | 29.010 | −17.462 | 1.00 | 21.62 | C |
| ATOM | 683 | CB | ASN | A | 90 | 1.414 | 29.220 | −18.716 | 1.00 | 22.59 | C |
| ATOM | 684 | CG | ASN | A | 90 | 0.716 | 30.562 | −18.737 | 1.00 | 23.18 | C |
| ATOM | 685 | OD1 | ASN | A | 90 | 0.464 | 31.166 | −17.695 | 1.00 | 23.09 | O |
| ATOM | 686 | ND2 | ASN | A | 90 | 0.394 | 31.037 | −19.935 | 1.00 | 21.28 | N |
| ATOM | 687 | C | ASN | A | 90 | 3.291 | 30.146 | −17.262 | 1.00 | 20.61 | C |
| ATOM | 688 | O | ASN | A | 90 | 4.123 | 30.393 | −18.131 | 1.00 | 19.35 | O |
| ATOM | 689 | N | LYS | A | 91 | 3.224 | 30.830 | −16.120 | 1.00 | 20.18 | N |
| ATOM | 690 | CA | LYS | A | 91 | 4.184 | 31.890 | −15.792 | 1.00 | 20.62 | C |
| ATOM | 691 | CB | LYS | A | 91 | 3.508 | 33.265 | −15.768 | 1.00 | 21.83 | C |
| ATOM | 692 | CG | LYS | A | 91 | 2.995 | 33.739 | −17.132 | 1.00 | 22.74 | C |
| ATOM | 693 | CD | LYS | A | 91 | 3.939 | 34.731 | −17.811 | 1.00 | 25.51 | C |

APPENDIX 1-continued

| | | | | | | | | | | | |
|---|---|---|---|---|---|---|---|---|---|---|---|
| ATOM | 694 | CE | LYS | A | 91 | 3.500 | 35.008 | −19.248 | 1.00 | 28.49 | C |
| ATOM | 695 | NZ | LYS | A | 91 | 3.757 | 36.414 | −19.675 | 1.00 | 30.57 | N |
| ATOM | 696 | C | LYS | A | 91 | 4.839 | 31.559 | −14.447 | 1.00 | 21.15 | C |
| ATOM | 697 | O | LYS | A | 91 | 4.158 | 31.154 | −13.506 | 1.00 | 19.94 | O |
| ATOM | 698 | N | SER | A | 92 | 6.155 | 31.734 | −14.359 | 1.00 | 20.82 | N |
| ATOM | 699 | CA | SER | A | 92 | 6.918 | 31.308 | −13.179 | 1.00 | 22.01 | C |
| ATOM | 700 | CB | SER | A | 92 | 8.420 | 31.449 | −13.440 | 1.00 | 21.23 | C |
| ATOM | 701 | OG | SER | A | 92 | 8.777 | 32.804 | −13.657 | 1.00 | 21.35 | O |
| ATOM | 702 | C | SER | A | 92 | 6.559 | 32.018 | −11.877 | 1.00 | 22.28 | C |
| ATOM | 703 | O | SER | A | 92 | 6.937 | 31.583 | −10.792 | 1.00 | 22.45 | O |
| ATOM | 704 | N | GLN | A | 93 | 5.807 | 33.098 | −12.006 | 1.00 | 22.36 | N |
| ATOM | 705 | CA | GLN | A | 93 | 5.441 | 33.975 | −10.906 | 1.00 | 23.73 | C |
| ATOM | 706 | CB | GLN | A | 93 | 4.982 | 35.266 | −11.557 | 1.00 | 25.56 | C |
| ATOM | 707 | CG | GLN | A | 93 | 5.433 | 35.222 | −13.015 | 1.00 | 29.43 | C |
| ATOM | 708 | CD | GLN | A | 93 | 5.048 | 36.419 | −13.837 | 1.00 | 33.72 | C |
| ATOM | 709 | OE1 | GLN | A | 93 | 3.981 | 36.998 | −13.647 | 1.00 | 35.59 | O |
| ATOM | 710 | NE2 | GLN | A | 93 | 5.911 | 36.785 | −14.777 | 1.00 | 37.81 | N |
| ATOM | 711 | C | GLN | A | 93 | 4.357 | 33.374 | −10.013 | 1.00 | 22.06 | C |
| ATOM | 712 | O | GLN | A | 93 | 4.135 | 33.830 | −8.888 | 1.00 | 19.00 | O |
| ATOM | 713 | N | TYR | A | 94 | 3.687 | 32.347 | −10.528 | 1.00 | 22.03 | N |
| ATOM | 714 | CA | TYR | A | 94 | 2.668 | 31.631 | −9.771 | 1.00 | 22.48 | C |
| ATOM | 715 | CB | TYR | A | 94 | 1.269 | 31.861 | −10.345 | 1.00 | 22.29 | C |
| ATOM | 716 | CG | TYR | A | 94 | 0.912 | 33.322 | −10.342 | 1.00 | 25.27 | C |
| ATOM | 717 | CD1 | TYR | A | 94 | 1.057 | 34.087 | −11.487 | 1.00 | 23.39 | C |
| ATOM | 718 | CE1 | TYR | A | 94 | 0.757 | 35.429 | −11.488 | 1.00 | 26.39 | C |
| ATOM | 719 | CZ | TYR | A | 94 | 0.316 | 36.029 | −10.328 | 1.00 | 26.49 | C |
| ATOM | 720 | OH | TYR | A | 94 | 0.016 | 37.370 | −10.332 | 1.00 | 29.72 | O |
| ATOM | 721 | CE2 | TYR | A | 94 | 0.174 | 35.293 | −9.171 | 1.00 | 25.15 | C |
| ATOM | 722 | CD2 | TYR | A | 94 | 0.478 | 33.948 | −9.181 | 1.00 | 22.81 | C |
| ATOM | 723 | C | TYR | A | 94 | 3.016 | 30.156 | −9.695 | 1.00 | 22.66 | C |
| ATOM | 724 | O | TYR | A | 94 | 3.698 | 29.612 | −10.566 | 1.00 | 21.05 | O |
| ATOM | 725 | N | GLU | A | 95 | 2.515 | 29.526 | −8.643 | 1.00 | 23.58 | N |
| ATOM | 726 | CA | GLU | A | 95 | 2.858 | 28.172 | −8.272 | 1.00 | 25.71 | C |
| ATOM | 727 | CB | GLU | A | 95 | 3.845 | 28.302 | −7.114 | 1.00 | 27.10 | C |
| ATOM | 728 | CG | GLU | A | 95 | 4.926 | 27.255 | −6.935 | 1.00 | 34.72 | C |
| ATOM | 729 | CD | GLU | A | 95 | 5.492 | 27.329 | −5.528 | 1.00 | 44.27 | C |
| ATOM | 730 | OE1 | GLU | A | 95 | 6.286 | 28.253 | −5.241 | 1.00 | 46.74 | O |
| ATOM | 731 | OE2 | GLU | A | 95 | 5.106 | 26.486 | −4.693 | 1.00 | 47.77 | O |
| ATOM | 732 | C | GLU | A | 95 | 1.583 | 27.543 | −7.732 | 1.00 | 25.85 | C |
| ATOM | 733 | O | GLU | A | 95 | 0.818 | 28.213 | −7.041 | 1.00 | 24.94 | O |
| ATOM | 734 | N | ILE | A | 96 | 1.338 | 26.270 | −8.029 | 1.00 | 23.73 | N |
| ATOM | 735 | CA | ILE | A | 96 | 0.178 | 25.591 | −7.452 | 1.00 | 24.08 | C |
| ATOM | 736 | CB | ILE | A | 96 | −0.741 | 25.000 | −8.536 | 1.00 | 24.17 | C |
| ATOM | 737 | CG1 | ILE | A | 96 | −1.363 | 26.102 | −9.388 | 1.00 | 21.98 | C |
| ATOM | 738 | CD1 | ILE | A | 96 | −0.539 | 26.449 | −10.594 | 1.00 | 21.05 | C |
| ATOM | 739 | CG2 | ILE | A | 96 | −1.821 | 24.131 | −7.896 | 1.00 | 22.07 | C |
| ATOM | 740 | C | ILE | A | 96 | 0.566 | 24.454 | −6.520 | 1.00 | 24.93 | C |
| ATOM | 741 | O | ILE | A | 96 | 1.389 | 23.611 | −6.871 | 1.00 | 24.71 | O |
| ATOM | 742 | N | ILE | A | 97 | −0.033 | 24.425 | −5.334 | 1.00 | 24.49 | N |
| ATOM | 743 | CA | ILE | A | 97 | 0.145 | 23.284 | −4.450 | 1.00 | 24.95 | C |
| ATOM | 744 | CB | ILE | A | 97 | 0.240 | 23.708 | −2.985 | 1.00 | 25.07 | C |
| ATOM | 745 | CG1 | ILE | A | 97 | 1.347 | 24.744 | −2.808 | 1.00 | 26.12 | C |
| ATOM | 746 | CD1 | ILE | A | 97 | 1.587 | 25.126 | −1.372 | 1.00 | 28.90 | C |
| ATOM | 747 | CG2 | ILE | A | 97 | 0.505 | 22.493 | −2.105 | 1.00 | 25.26 | C |
| ATOM | 748 | C | ILE | A | 97 | −1.035 | 22.344 | −4.655 | 1.00 | 25.56 | C |
| ATOM | 749 | O | ILE | A | 97 | −2.193 | 22.766 | −4.624 | 1.00 | 25.85 | O |
| ATOM | 750 | N | THR | A | 98 | −0.733 | 21.073 | −4.869 | 1.00 | 26.48 | N |
| ATOM | 751 | CA | THR | A | 98 | −1.760 | 20.078 | −5.131 | 1.00 | 26.12 | C |
| ATOM | 752 | CB | THR | A | 98 | −1.566 | 19.495 | −6.538 | 1.00 | 27.13 | C |
| ATOM | 753 | OG1 | THR | A | 98 | −1.737 | 20.525 | −7.517 | 1.00 | 30.30 | O |
| ATOM | 754 | CG2 | THR | A | 98 | −2.671 | 18.500 | −6.860 | 1.00 | 27.06 | C |
| ATOM | 755 | C | THR | A | 98 | −1.736 | 18.928 | −4.143 | 1.00 | 26.04 | C |
| ATOM | 756 | O | THR | A | 98 | −0.762 | 18.181 | −4.076 | 1.00 | 25.26 | O |
| ATOM | 757 | N | GLN | A | 99 | −2.804 | 18.784 | −3.371 | 1.00 | 25.89 | N |
| ATOM | 758 | CA | GLN | A | 99 | −2.936 | 17.613 | −2.520 | 1.00 | 27.34 | C |
| ATOM | 759 | CB | GLN | A | 99 | −2.498 | 17.874 | −1.083 | 1.00 | 29.07 | C |
| ATOM | 760 | CG | GLN | A | 99 | −3.374 | 18.799 | −0.293 | 1.00 | 35.42 | C |
| ATOM | 761 | CD | GLN | A | 99 | −2.568 | 19.548 | 0.732 | 1.00 | 44.28 | C |
| ATOM | 762 | OE1 | GLN | A | 99 | −1.350 | 19.383 | 0.800 | 1.00 | 47.59 | O |
| ATOM | 763 | NE2 | GLN | A | 99 | −3.230 | 20.380 | 1.524 | 1.00 | 50.15 | N |
| ATOM | 764 | C | GLN | A | 99 | −4.353 | 17.081 | −2.599 | 1.00 | 27.53 | C |
| ATOM | 765 | O | GLN | A | 99 | −5.314 | 17.740 | −2.198 | 1.00 | 26.16 | O |
| ATOM | 766 | N | GLY | A | 100 | −4.467 | 15.882 | −3.150 | 1.00 | 27.07 | N |
| ATOM | 767 | CA | GLY | A | 100 | −5.756 | 15.267 | −3.351 | 1.00 | 29.12 | C |
| ATOM | 768 | C | GLY | A | 100 | −5.809 | 13.841 | −2.870 | 1.00 | 29.52 | C |
| ATOM | 769 | O | GLY | A | 100 | −4.792 | 13.153 | −2.766 | 1.00 | 28.98 | O |
| ATOM | 770 | N | GLY | A | 101 | −7.028 | 13.393 | −2.609 | 1.00 | 30.03 | N |
| ATOM | 771 | CA | GLY | A | 101 | −7.257 | 12.086 | −2.046 | 1.00 | 30.82 | C |
| ATOM | 772 | C | GLY | A | 101 | −7.296 | 10.884 | −2.960 | 1.00 | 32.07 | C |
| ATOM | 773 | O | GLY | A | 101 | −7.501 | 10.960 | −4.174 | 1.00 | 29.69 | O |

APPENDIX 1-continued

| | | | | | | | | | | | |
|---|---|---|---|---|---|---|---|---|---|---|---|
| ATOM | 774 | N | SER | A | 102 | −7.087 | 9.785 | −2.276 | 1.00 | 34.25 | N |
| ATOM | 775 | CA | SER | A | 102 | −7.125 | 8.468 | −2.825 | 1.00 | 36.02 | C |
| ATOM | 776 | CB | SER | A | 102 | −6.193 | 7.556 | −2.040 | 1.00 | 36.55 | C |
| ATOM | 777 | OG | SER | A | 102 | −6.010 | 8.024 | −0.722 | 1.00 | 39.12 | O |
| ATOM | 778 | C | SER | A | 102 | −8.563 | 8.000 | −2.713 | 1.00 | 35.90 | C |
| ATOM | 779 | O | SER | A | 102 | −9.343 | 8.647 | −2.018 | 1.00 | 35.23 | O |
| ATOM | 780 | N | GLY | A | 103 | −8.986 | 6.930 | −3.365 | 1.00 | 37.33 | N |
| ATOM | 781 | CA | GLY | A | 103 | −10.352 | 6.532 | −3.114 | 1.00 | 37.60 | C |
| ATOM | 782 | C | GLY | A | 103 | −11.382 | 6.699 | −4.242 | 1.00 | 38.60 | C |
| ATOM | 783 | O | GLY | A | 103 | −11.059 | 6.692 | −5.432 | 1.00 | 38.63 | O |
| ATOM | 784 | N | ASN | A | 104 | −12.630 | 6.838 | −3.815 | 1.00 | 38.81 | N |
| ATOM | 785 | CA | ASN | A | 104 | −13.793 | 6.857 | −4.707 | 1.00 | 38.65 | C |
| ATOM | 786 | CB | ASN | A | 104 | −14.664 | 5.667 | −4.347 | 1.00 | 39.50 | C |
| ATOM | 787 | CG | ASN | A | 104 | −15.731 | 5.451 | −5.372 | 1.00 | 42.05 | C |
| ATOM | 788 | OD1 | ASN | A | 104 | −15.831 | 6.200 | −6.336 | 1.00 | 51.15 | O |
| ATOM | 789 | ND2 | ASN | A | 104 | −16.528 | 4.419 | −5.186 | 1.00 | 45.02 | N |
| ATOM | 790 | C | ASN | A | 104 | −14.564 | 8.165 | −4.687 | 1.00 | 37.26 | C |
| ATOM | 791 | O | ASN | A | 104 | −14.755 | 8.806 | −5.733 | 1.00 | 39.29 | O |
| ATOM | 792 | N | GLN | A | 105 | −15.023 | 8.554 | −3.500 | 1.00 | 34.32 | N |
| ATOM | 793 | CA | GLN | A | 105 | −15.589 | 9.893 | −3.351 | 1.00 | 31.80 | C |
| ATOM | 794 | CB | GLN | A | 105 | −16.652 | 10.016 | −2.251 | 1.00 | 31.93 | C |
| ATOM | 795 | CG | GLN | A | 105 | −18.006 | 9.358 | −2.498 | 1.00 | 27.94 | C |
| ATOM | 796 | CD | GLN | A | 105 | −18.915 | 9.453 | −1.266 | 1.00 | 25.21 | C |
| ATOM | 797 | OE1 | GLN | A | 105 | −18.712 | 8.763 | −0.285 | 1.00 | 22.71 | O |
| ATOM | 798 | NE2 | GLN | A | 105 | −19.978 | 10.255 | −1.128 | 1.00 | 24.00 | N |
| ATOM | 799 | C | GLN | A | 105 | −14.336 | 10.676 | −2.933 | 1.00 | 31.46 | C |
| ATOM | 800 | O | GLN | A | 105 | −14.035 | 10.784 | −1.743 | 1.00 | 31.00 | O |
| ATOM | 801 | N | SER | A | 106 | −13.594 | 11.236 | −3.894 | 1.00 | 29.69 | N |
| ATOM | 802 | CA | SER | A | 106 | −12.336 | 11.860 | −3.487 | 1.00 | 28.53 | C |
| ATOM | 803 | CB | SER | A | 106 | −11.203 | 11.262 | −4.302 | 1.00 | 27.95 | C |
| ATOM | 804 | OG | SER | A | 106 | −11.201 | 11.780 | −5.616 | 1.00 | 30.97 | O |
| ATOM | 805 | C | SER | A | 106 | −12.273 | 13.375 | −3.493 | 1.00 | 27.39 | C |
| ATOM | 806 | O | SER | A | 106 | −13.071 | 14.071 | −4.127 | 1.00 | 28.69 | O |
| ATOM | 807 | N | HIS | A | 107 | −11.297 | 13.867 | −2.743 | 1.00 | 25.64 | N |
| ATOM | 808 | CA | HIS | A | 107 | −11.133 | 15.290 | −2.536 | 1.00 | 25.50 | C |
| ATOM | 809 | CB | HIS | A | 107 | −11.417 | 15.601 | −1.067 | 1.00 | 25.52 | C |
| ATOM | 810 | CG | HIS | A | 107 | −12.176 | 16.870 | −0.848 | 1.00 | 29.94 | C |
| ATOM | 811 | ND1 | HIS | A | 107 | −13.478 | 16.889 | −0.395 | 1.00 | 30.47 | N |
| ATOM | 812 | CE1 | HIS | A | 107 | −13.887 | 18.140 | −0.289 | 1.00 | 36.42 | C |
| ATOM | 813 | NE2 | HIS | A | 107 | −12.897 | 18.934 | −0.654 | 1.00 | 39.36 | N |
| ATOM | 814 | CD2 | HIS | A | 107 | −11.814 | 18.165 | −1.006 | 1.00 | 35.04 | C |
| ATOM | 815 | C | HIS | A | 107 | −9.729 | 15.758 | −2.889 | 1.00 | 23.45 | C |
| ATOM | 816 | O | HIS | A | 107 | −8.741 | 15.124 | −2.522 | 1.00 | 23.20 | O |
| ATOM | 817 | N | VAL | A | 108 | −9.650 | 16.871 | −3.608 | 1.00 | 22.60 | N |
| ATOM | 818 | CA | VAL | A | 108 | −8.366 | 17.466 | −3.947 | 1.00 | 23.16 | C |
| ATOM | 819 | CB | VAL | A | 108 | −7.963 | 17.205 | −5.419 | 1.00 | 23.67 | C |
| ATOM | 820 | CG1 | VAL | A | 108 | −9.056 | 17.657 | −6.374 | 1.00 | 19.49 | C |
| ATOM | 821 | CG2 | VAL | A | 108 | −6.634 | 17.885 | −5.747 | 1.00 | 24.42 | C |
| ATOM | 822 | C | VAL | A | 108 | −8.397 | 18.962 | −3.673 | 1.00 | 23.19 | C |
| ATOM | 823 | O | VAL | A | 108 | −9.392 | 19.636 | −3.947 | 1.00 | 22.31 | O |
| ATOM | 824 | N | THR | A | 109 | −7.312 | 19.471 | −3.101 | 1.00 | 23.42 | N |
| ATOM | 825 | CA | THR | A | 109 | −7.188 | 20.898 | −2.854 | 1.00 | 23.93 | C |
| ATOM | 826 | CB | THR | A | 109 | −6.990 | 21.183 | −1.353 | 1.00 | 24.81 | C |
| ATOM | 827 | OG1 | THR | A | 109 | −8.164 | 20.791 | −0.633 | 1.00 | 25.76 | O |
| ATOM | 828 | CG2 | THR | A | 109 | −6.917 | 22.679 | −1.101 | 1.00 | 24.77 | C |
| ATOM | 829 | C | THR | A | 109 | −6.042 | 21.496 | −3.666 | 1.00 | 23.53 | C |
| ATOM | 830 | O | THR | A | 109 | −4.908 | 21.020 | −3.616 | 1.00 | 23.96 | O |
| ATOM | 831 | N | TYR | A | 110 | −6.363 | 22.537 | −4.430 | 1.00 | 23.10 | N |
| ATOM | 832 | CA | TYR | A | 110 | −5.374 | 23.280 | −5.199 | 1.00 | 22.02 | C |
| ATOM | 833 | CB | TYR | A | 110 | −5.856 | 23.506 | −6.627 | 1.00 | 22.66 | C |
| ATOM | 834 | CG | TYR | A | 110 | −6.201 | 22.260 | −7.401 | 1.00 | 25.02 | C |
| ATOM | 835 | CD1 | TYR | A | 110 | −7.524 | 21.882 | −7.583 | 1.00 | 21.75 | C |
| ATOM | 836 | CE1 | TYR | A | 110 | −7.849 | 20.755 | −8.303 | 1.00 | 21.69 | C |
| ATOM | 837 | CZ | TYR | A | 110 | −6.847 | 19.990 | −8.858 | 1.00 | 22.49 | C |
| ATOM | 838 | OH | TYR | A | 110 | −7.171 | 18.863 | −9.576 | 1.00 | 23.78 | O |
| ATOM | 839 | CE2 | TYR | A | 110 | −5.525 | 20.348 | −8.698 | 1.00 | 22.23 | C |
| ATOM | 840 | CD2 | TYR | A | 110 | −5.209 | 21.478 | −7.976 | 1.00 | 22.38 | C |
| ATOM | 841 | C | TYR | A | 110 | −5.174 | 24.644 | −4.551 | 1.00 | 21.65 | C |
| ATOM | 842 | O | TYR | A | 110 | −6.114 | 25.430 | −4.450 | 1.00 | 19.62 | O |
| ATOM | 843 | N | THR | A | 111 | −3.956 | 24.928 | −4.111 | 1.00 | 20.52 | N |
| ATOM | 844 | CA | THR | A | 111 | −3.670 | 26.218 | −3.504 | 1.00 | 20.25 | C |
| ATOM | 845 | CB | THR | A | 111 | −2.942 | 26.036 | −2.152 | 1.00 | 22.42 | C |
| ATOM | 846 | OG1 | THR | A | 111 | −3.807 | 25.340 | −1.243 | 1.00 | 21.55 | O |
| ATOM | 847 | CG2 | THR | A | 111 | −2.730 | 27.373 | −1.458 | 1.00 | 23.51 | C |
| ATOM | 848 | C | THR | A | 111 | −2.864 | 27.019 | −4.520 | 1.00 | 20.64 | C |
| ATOM | 849 | O | THR | A | 111 | −1.736 | 26.658 | −4.858 | 1.00 | 19.47 | O |
| ATOM | 850 | N | ILE | A | 112 | −3.479 | 28.069 | −5.057 | 1.00 | 18.73 | N |
| ATOM | 851 | CA | ILE | A | 112 | −2.831 | 28.887 | −6.074 | 1.00 | 20.13 | C |
| ATOM | 852 | CB | ILE | A | 112 | −3.841 | 29.484 | −7.071 | 1.00 | 21.04 | C |
| ATOM | 853 | CG1 | ILE | A | 112 | −5.043 | 28.556 | −7.264 | 1.00 | 18.50 | C |

APPENDIX 1-continued

| | | | | | | | | | | | |
|---|---|---|---|---|---|---|---|---|---|---|---|
| ATOM | 854 | CD1 | ILE | A | 112 | −4.681 | 27.150 | −7.686 | 1.00 | 20.39 | C |
| ATOM | 855 | CG2 | ILE | A | 112 | −3.152 | 29.784 | −8.399 | 1.00 | 22.39 | C |
| ATOM | 856 | C | ILE | A | 112 | −2.095 | 30.004 | −5.385 | 1.00 | 21.15 | C |
| ATOM | 857 | O | ILE | A | 112 | −2.705 | 30.885 | −4.783 | 1.00 | 21.07 | O |
| ATOM | 858 | N | GLN | A | 113 | −0.777 | 29.983 | −5.485 | 1.00 | 18.89 | N |
| ATOM | 859 | CA | GLN | A | 113 | −0.012 | 30.967 | −4.760 | 1.00 | 21.47 | C |
| ATOM | 860 | CB | GLN | A | 113 | 0.627 | 30.316 | −3.539 | 1.00 | 20.84 | C |
| ATOM | 861 | CG | GLN | A | 113 | 1.638 | 29.256 | −3.907 | 1.00 | 28.15 | C |
| ATOM | 862 | CD | GLN | A | 113 | 2.153 | 28.503 | −2.707 | 1.00 | 28.39 | C |
| ATOM | 863 | OE1 | GLN | A | 113 | 1.617 | 28.634 | −1.607 | 1.00 | 30.14 | O |
| ATOM | 864 | NE2 | GLN | A | 113 | 3.196 | 27.709 | −2.911 | 1.00 | 25.13 | N |
| ATOM | 865 | C | GLN | A | 113 | 1.065 | 31.673 | −5.545 | 1.00 | 21.44 | C |
| ATOM | 866 | O | GLN | A | 113 | 1.395 | 31.341 | −6.686 | 1.00 | 20.90 | O |
| ATOM | 867 | N | THR | A | 114 | 1.593 | 32.676 | −4.866 | 1.00 | 21.33 | N |
| ATOM | 868 | CA | THR | A | 114 | 2.691 | 33.487 | −5.311 | 1.00 | 24.29 | C |
| ATOM | 869 | CB | THR | A | 114 | 2.755 | 34.811 | −4.549 | 1.00 | 23.47 | C |
| ATOM | 870 | OG1 | THR | A | 114 | 2.945 | 34.553 | −3.153 | 1.00 | 30.54 | O |
| ATOM | 871 | CG2 | THR | A | 114 | 1.464 | 35.594 | −4.733 | 1.00 | 27.33 | C |
| ATOM | 872 | C | THR | A | 114 | 3.948 | 32.645 | −5.153 | 1.00 | 22.90 | C |
| ATOM | 873 | O | THR | A | 114 | 4.111 | 31.958 | −4.145 | 1.00 | 23.43 | O |
| ATOM | 874 | N | THR | A | 115 | 4.829 | 32.665 | −6.146 | 1.00 | 21.93 | N |
| ATOM | 875 | CA | THR | A | 115 | 6.031 | 31.847 | −6.056 | 1.00 | 23.25 | C |
| ATOM | 876 | CB | THR | A | 115 | 6.693 | 31.672 | −7.423 | 1.00 | 24.35 | C |
| ATOM | 877 | OG1 | THR | A | 115 | 5.779 | 31.034 | −8.322 | 1.00 | 27.30 | O |
| ATOM | 878 | CG2 | THR | A | 115 | 7.944 | 30.815 | −7.303 | 1.00 | 22.44 | C |
| ATOM | 879 | C | THR | A | 115 | 7.025 | 32.470 | −5.084 | 1.00 | 22.76 | C |
| ATOM | 880 | O | THR | A | 115 | 7.145 | 33.692 | −4.998 | 1.00 | 22.71 | O |
| ATOM | 881 | N | SER | A | 116 | 7.710 | 31.626 | −4.325 | 1.00 | 21.39 | N |
| ATOM | 882 | CA | SER | A | 116 | 8.687 | 32.111 | −3.365 | 1.00 | 23.10 | C |
| ATOM | 883 | CB | SER | A | 116 | 8.579 | 31.354 | −2.044 | 1.00 | 22.58 | C |
| ATOM | 884 | OG | SER | A | 116 | 7.421 | 31.740 | −1.329 | 1.00 | 20.00 | O |
| ATOM | 885 | C | SER | A | 116 | 10.076 | 31.951 | −3.938 | 1.00 | 23.62 | C |
| ATOM | 886 | O | SER | A | 116 | 10.294 | 31.154 | −4.850 | 1.00 | 22.16 | O |
| ATOM | 887 | N | SER | A | 117 | 11.022 | 32.713 | −3.411 | 1.00 | 24.19 | N |
| ATOM | 888 | CA | SER | A | 117 | 12.380 | 32.605 | −3.901 | 1.00 | 25.55 | C |
| ATOM | 889 | CB | SER | A | 117 | 13.042 | 33.978 | −4.032 | 1.00 | 25.43 | C |
| ATOM | 890 | OG | SER | A | 117 | 13.961 | 34.208 | −2.981 | 1.00 | 27.71 | O |
| ATOM | 891 | C | SER | A | 117 | 13.174 | 31.693 | −2.982 | 1.00 | 25.15 | C |
| ATOM | 892 | O | SER | A | 117 | 13.219 | 31.887 | −1.767 | 1.00 | 24.64 | O |
| ATOM | 893 | N | ARG | A | 118 | 13.793 | 30.689 | −3.583 | 1.00 | 24.99 | N |
| ATOM | 894 | CA | ARG | A | 118 | 14.577 | 29.708 | −2.857 | 1.00 | 25.50 | C |
| ATOM | 895 | CB | ARG | A | 118 | 14.675 | 28.442 | −3.707 | 1.00 | 26.03 | C |
| ATOM | 896 | CG | ARG | A | 118 | 15.157 | 27.214 | −2.979 | 1.00 | 27.66 | C |
| ATOM | 897 | CD | ARG | A | 118 | 14.905 | 25.928 | −3.743 | 1.00 | 33.83 | C |
| ATOM | 898 | NE | ARG | A | 118 | 13.724 | 25.209 | −3.270 | 1.00 | 32.39 | N |
| ATOM | 899 | CZ | ARG | A | 118 | 12.605 | 25.059 | −3.968 | 1.00 | 39.89 | C |
| ATOM | 900 | NH1 | ARG | A | 118 | 12.498 | 25.587 | −5.180 | 1.00 | 43.31 | N |
| ATOM | 901 | NH2 | ARG | A | 118 | 11.590 | 24.376 | −3.455 | 1.00 | 37.18 | N |
| ATOM | 902 | C | ARG | A | 118 | 15.978 | 30.208 | −2.486 | 1.00 | 25.23 | C |
| ATOM | 903 | O | ARG | A | 118 | 16.667 | 30.824 | −3.299 | 1.00 | 25.07 | O |
| ATOM | 904 | N | TYR | A | 119 | 16.371 | 29.955 | −1.240 | 1.00 | 25.20 | N |
| ATOM | 905 | CA | TYR | A | 119 | 17.715 | 30.232 | −0.739 | 1.00 | 25.74 | C |
| ATOM | 906 | CB | TYR | A | 119 | 17.638 | 30.485 | 0.775 | 1.00 | 24.93 | C |
| ATOM | 907 | CG | TYR | A | 119 | 18.881 | 30.905 | 1.579 | 1.00 | 26.32 | C |
| ATOM | 908 | CD1 | TYR | A | 119 | 19.124 | 32.246 | 1.881 | 1.00 | 26.48 | C |
| ATOM | 909 | CE1 | TYR | A | 119 | 20.218 | 32.631 | 2.663 | 1.00 | 26.71 | C |
| ATOM | 910 | CZ | TYR | A | 119 | 21.065 | 31.671 | 3.180 | 1.00 | 28.22 | C |
| ATOM | 911 | OH | TYR | A | 119 | 22.142 | 32.049 | 3.952 | 1.00 | 30.00 | O |
| ATOM | 912 | CE2 | TYR | A | 119 | 20.831 | 30.334 | 2.923 | 1.00 | 27.78 | C |
| ATOM | 913 | CD2 | TYR | A | 119 | 19.735 | 29.956 | 2.140 | 1.00 | 25.89 | C |
| ATOM | 914 | C | TYR | A | 119 | 18.433 | 28.925 | −1.039 | 1.00 | 24.89 | C |
| ATOM | 915 | O | TYR | A | 119 | 19.657 | 28.851 | −1.065 | 1.00 | 28.03 | O |
| ATOM | 916 | O | HOH | W | 1 | −14.559 | 14.990 | 0.123 | 0.50 | 27.84 | O |
| ATOM | 917 | O | HOH | W | 2 | −3.227 | 22.536 | −1.713 | 1.00 | 24.73 | O |
| ATOM | 918 | O | HOH | W | 3 | 2.121 | 20.187 | −4.665 | 1.00 | 38.18 | O |
| ATOM | 919 | O | HOH | W | 4 | −11.411 | 30.080 | −22.842 | 1.00 | 30.93 | O |
| ATOM | 920 | O | HOH | W | 5 | −13.591 | 32.301 | −21.281 | 1.00 | 42.14 | O |
| ATOM | 921 | O | HOH | W | 6 | −2.445 | 23.591 | −19.928 | 1.00 | 36.28 | O |
| ATOM | 922 | O | HOH | W | 7 | −1.738 | 26.722 | −17.284 | 1.00 | 43.23 | O |
| ATOM | 923 | O | HOH | W | 8 | −18.754 | 29.155 | −21.318 | 1.00 | 45.28 | O |
| ATOM | 924 | O | HOH | W | 9 | 1.119 | 39.224 | −7.410 | 1.00 | 44.97 | O |
| ATOM | 925 | O | HOH | W | 10 | 0.534 | 33.622 | −2.189 | 1.00 | 32.51 | O |
| ATOM | 927 | O | HOH | W | 11 | 7.824 | 25.984 | −3.897 | 1.00 | 43.51 | O |
| ATOM | 928 | O | HOH | W | 12 | 19.203 | 30.879 | −5.626 | 1.00 | 44.10 | O |
| ATOM | 929 | O | HOH | W | 13 | −22.689 | 2.969 | −19.990 | 1.00 | 42.82 | O |
| ATOM | 930 | O | HOH | W | 14 | −7.161 | −0.951 | −10.204 | 1.00 | 38.86 | O |
| ATOM | 932 | O | HOH | W | 15 | −3.700 | 36.274 | −1.163 | 1.00 | 36.83 | O |
| ATOM | 933 | O | HOH | W | 16 | −23.572 | 24.381 | −10.521 | 1.00 | 37.83 | O |
| ATOM | 935 | O | HOH | W | 17 | −20.762 | 13.499 | −1.986 | 1.00 | 44.73 | O |
| ATOM | 936 | O | HOH | W | 18 | 18.058 | 32.923 | −5.866 | 1.00 | 38.33 | O |

APPENDIX 1-continued

| | | | | | | | | | | | |
|---|---|---|---|---|---|---|---|---|---|---|---|
| ATOM | 937 | O | HOH | W | 19 | 3.068 | 37.314 | −2.600 | 1.00 | 39.55 | O |
| ATOM | 938 | O | HOH | W | 20 | −5.029 | 22.918 | 2.276 | 1.00 | 36.67 | O |
| ATOM | 939 | O | HOH | W | 21 | 7.686 | 32.276 | −17.226 | 1.00 | 36.19 | O |
| ATOM | 940 | O | HOH | W | 22 | −10.310 | 39.058 | −5.931 | 1.00 | 39.25 | O |
| ATOM | 941 | O | HOH | W | 23 | 5.409 | 29.664 | −3.323 | 1.00 | 31.60 | O |
| ATOM | 942 | O | HOH | W | 24 | −3.061 | 2.513 | −9.205 | 1.00 | 42.76 | O |
| ATOM | 943 | O | HOH | W | 25 | −17.878 | 8.534 | −16.806 | 1.00 | 38.00 | O |
| ATOM | 944 | O | HOH | W | 26 | −14.466 | 32.442 | −24.824 | 1.00 | 42.24 | O |
| ATOM | 945 | O | HOH | W | 27 | −17.952 | 26.616 | −2.086 | 1.00 | 38.39 | O |
| ATOM | 946 | O | HOH | W | 28 | −7.866 | 41.166 | −9.335 | 1.00 | 37.60 | O |
| ATOM | 947 | O | HOH | W | 29 | −5.147 | 25.608 | 0.944 | 1.00 | 26.31 | O |
| ATOM | 948 | O | HOH | W | 30 | 3.398 | 25.915 | −12.359 | 1.00 | 42.41 | O |
| ATOM | 950 | O | HOH | W | 31 | 3.685 | 17.090 | −11.869 | 1.00 | 43.77 | O |
| ATOM | 952 | O | HOH | W | 32 | −6.148 | 2.482 | −6.226 | 1.00 | 45.41 | O |
| ATOM | 953 | O | HOH | W | 33 | −1.142 | 26.694 | −20.196 | 1.00 | 46.61 | O |
| ATOM | 954 | O | HOH | W | 34 | −5.285 | 32.131 | −22.226 | 1.00 | 43.31 | O |
| ATOM | 955 | O | HOH | W | 35 | −11.273 | 41.495 | −9.609 | 1.00 | 35.70 | O |
| ATOM | 956 | O | HOH | W | 36 | −5.031 | 44.491 | −12.001 | 1.00 | 36.83 | O |
| ATOM | 957 | O | HOH | W | 37 | −7.969 | 25.331 | 1.388 | 1.00 | 44.78 | O |
| ATOM | 958 | O | HOH | W | 38 | 3.127 | 24.741 | −9.731 | 1.00 | 39.57 | O |
| ATOM | 959 | O | HOH | W | 39 | 20.331 | 30.525 | −1.815 | 1.00 | 38.12 | O |
| ATOM | 960 | O | HOH | W | 40 | −15.691 | 35.326 | −5.763 | 1.00 | 45.12 | O |
| ATOM | 961 | O | HOH | W | 41 | 9.232 | 23.005 | −2.062 | 1.00 | 36.89 | O |
| ATOM | 962 | O | HOH | W | 42 | 5.969 | 28.000 | −14.974 | 1.00 | 41.48 | O |
| ATOM | 963 | O | HOH | W | 43 | 3.257 | 41.375 | −6.139 | 1.00 | 42.08 | O |
| ATOM | 964 | O | HOH | W | 44 | 5.399 | 27.827 | −11.600 | 1.00 | 45.55 | O |
| ATOM | 965 | O | HOH | W | 45 | 0.775 | 21.354 | −8.403 | 1.00 | 37.66 | O |
| ATOM | 967 | O | HOH | W | 46 | −21.248 | 26.695 | −8.253 | 1.00 | 40.43 | O |
| ATOM | 968 | O | HOH | W | 47 | −8.574 | 41.852 | −5.684 | 1.00 | 40.41 | O |
| ATOM | 969 | O | HOH | W | 48 | −24.659 | 23.245 | −6.310 | 1.00 | 40.25 | O |
| ATOM | 970 | O | HOH | W | 49 | −17.132 | 6.949 | −0.155 | 1.00 | 39.44 | O |
| ATOM | 972 | O | HOH | W | 50 | −3.415 | 28.071 | −24.096 | 1.00 | 44.88 | O |
| ATOM | 973 | O | HOH | W | 51 | −20.139 | 22.500 | −2.785 | 1.00 | 44.66 | O |
| ATOM | 974 | O | HOH | W | 52 | −0.986 | 37.218 | −2.381 | 1.00 | 44.32 | O |
| ATOM | 976 | O | HOH | W | 53 | −22.382 | 3.698 | −22.564 | 1.00 | 42.32 | O |
| ATOM | 979 | O | HOH | W | 54 | 8.478 | 38.108 | −4.765 | 1.00 | 40.63 | O |
| ATOM | 982 | O | HOH | W | 55 | −19.946 | 7.127 | −4.521 | 1.00 | 43.21 | O |
| ATOM | 984 | O | HOH | W | 56 | 6.496 | 39.021 | −16.893 | 1.00 | 44.40 | O |
| ATOM | 985 | O | HOH | W | 57 | −17.455 | 18.329 | −1.316 | 1.00 | 46.16 | O |
| ATOM | 987 | O | HOH | W | 58 | −12.524 | 33.301 | −24.061 | 1.00 | 40.56 | O |
| ATOM | 988 | O | HOH | W | 59 | 6.414 | 37.040 | −4.985 | 1.00 | 40.47 | O |
| ATOM | 989 | O | HOH | W | 60 | −9.023 | 34.535 | −20.227 | 1.00 | 44.58 | O |
| ATOM | 990 | O | HOH | W | 61 | −27.464 | 22.652 | −5.829 | 1.00 | 38.44 | O |
| ATOM | 991 | O | HOH | W | 62 | −26.909 | 14.965 | −7.893 | 1.00 | 41.51 | O |
| ATOM | 992 | O | HOH | W | 63 | −24.626 | 6.229 | −11.331 | 1.00 | 45.20 | O |
| ATOM | 993 | O | HOH | W | 64 | −17.082 | 24.917 | −19.027 | 1.00 | 42.52 | O |
| ATOM | 994 | O | HOH | W | 65 | −3.009 | 28.610 | −26.134 | 1.00 | 41.64 | O |
| ATOM | 995 | O | HOH | W | 66 | −15.913 | 17.226 | −27.554 | 1.00 | 41.28 | O |
| ATOM | 996 | O | HOH | W | 67 | 3.707 | 23.828 | −13.461 | 1.00 | 41.38 | O |

APPENDIX 2

PLOTSIMILARITY of: /ul/home/burmeist/projects/binaries/14kD/14kDrops.msf(*) from: 1 to: 133
Window: 1
Scoring matrix: GenRunData: blosum62.cmp
March 28, 2002 15:28
Accessible: 0 < 30%, 1 >= 30%, 2 >= 50%, 3 >= 80%
Out-facing: 0 not, 1 sort of, 2 obvious
B-factor: <=20,

| Position | Consensus | Cry34Ab1 | Obs sub-stitutions (-* invariant) | Sub-stitutions | Similarity Value | Acc | Out-facing | B-factor 0-5 cool to hot | B-factor residue avg from PDB file |
|---|---|---|---|---|---|---|---|---|---|
| 1 | M | M | — | ML(IV)(FQ) | 5.0 | — | | — | — |
| 2 | S | S | — | S(TNA)(DEGKQ) | 4.0 | — | | — | — |
| 3 | A | A | — | AGS\|T(VC)EQP | 4.0 | 2 | 2 | 2 | 31.14 |
| 4 | R | R | — | RKQN\|(HE)G(SA) | 5.0 | 0 | 1 | 3 | 34.86 |
| 5 | E | E | — | EQDKR(HNS) | 5.0 | 0 | 2 | 5 | 36.48 |
| 6 | V | V | — | VILM\|(AT) | 4.0 | 0 | 0 | 1 | 24.20 |
| 7 | H | H | — | HYN | 8.0 | 0 | 2 | 1 | 21.39 |
| 8 | I | I | — | IVL | 4.0 | 0 | 0 | 1 | 22.99 |
| 9 | E | D | | DEQNS\|KH | 2.8 | 0 | 2 | 1 | 24.03 |
| 10 | I | V | | VILM\|ATPCY | 3.4 | 0 | 0 | 1 | 23.49 |
| 11 | N | N | I | NS(HD)\|T(QRE) | 2.4 | 0 | 2 | 1 | 21.80 |

APPENDIX 2-continued

PLOTSIMILARITY of: /ul/home/burmeist/projects/binaries/14kD/14kDrops.msf(*) from: 1 to: 133
Window: 1
Scoring matrix: GenRunData: blosum62.cmp
March 28, 2002 15:28
Accessible: 0 < 30%, 1 >= 30%, 2 >= 50%, 3 >= 80%
Out-facing: 0 not, 1 sort of, 2 obvious
B-factor: <=20,

| Position | Consensus | Cry34Ab1 | Obs sub-stitutions (-* invariant) | Sub-stitutions | Similarity Value | Acc | Out-facing | B-factor 0-5 cool to hot | B-factor residue avg from PDB file |
|---|---|---|---|---|---|---|---|---|---|
| 12 | N | N | — | N(DSH)(EGKQT) | 6.0 | 0 | 0 | 1 | 21.90 |
| 13 | K | K | H | KR(QE)N\|SH | 2.8 | 1 | 2 | 1 | 21.76 |
| 14 | T | T | — | TS(VN) | 5.0 | 0 | 0 | 1 | 22.87 |
| 15 | G | G | R | GN\|(AS)R | 1.9 | 0 | 2 | 1 | 26.60 |
| 16 | H | H | — | HYN | 8.0 | 0 | 2 | 2 | 29.89 |
| 17 | T | T | — | TS(ANV) | 5.0 | 0 | 2 | 1 | 26.99 |
| 18 | L | L | — | L(IM)VF | 4.0 | 0 | 0 | 1 | 24.62 |
| 19 | Q | Q | — | QE(RK)(SMND) | 5.0 | 1 | 2 | 1 | 23.34 |
| 20 | L | L | M | LMIV\|P(AT)C | 3.3 | 0 | 2 | 2 | 26.00 |
| 21 | E | E | D | EDQKNS\|HR | 3.9 | 0 | 2 | 3 | 31.91 |
| 22 | D | D | K | DENQ | 3.3 | 2 | 2 | 2 | 27.82 |
| 23 | K | K | R | KRQEN\|S | 3.8 | 1 | 2 | 2 | 28.57 |
| 24 | T | T | — | TS(VNA) | 5.0 | 0 | 1 | 1 | 24.63 |
| 25 | K | K | R | KRQEN\|S | 3.8 | 1 | 2 | 2 | 29.78 |
| 26 | L | L | — | L(MI)VF | 4.0 | 0 | 0 | 1 | 26.83 |
| 27 | D | D | S, A, T | DESNT\|QAGP | 1.2 | 1 | 2 | 2 | 30.83 |
| 28 | G | G | H S | GSN\|A | 2.9 | 0 | 1 | 1 | 26.65 |
| 29 | G | G | — | G(NSA) | 6.0 | 0 | 1 | 1 | 25.27 |
| 30 | R | R | E | RKE(NH) | 3.1 | 1 | 2 | 2 | 29.56 |
| 31 | W | W | — | WY | 11.0 | 0 | 0 | 2 | 26.87 |
| 32 | R | R | I | RKQ\|(NHE) | 1.9 | 1 | 2 | 2 | 27.54 |
| 33 | T | T | I | TSV\|ANI | 2.6 | 0 | 1 | 1 | 27.09 |
| 34 | S | S | T | ST(NA)\|(DEKQ)G | 2.9 | 0 | 2 | 1 | 26.59 |
| 35 | P | P | — | P | 7.0 | 0 | 0 | 1 | 26.11 |
| 36 | T | T | V | TSVA\|(N) | 3.0 | 0 | 2 | 2 | 26.81 |
| 37 | N | N | — | N(DHS)(EGKQRT) | 6.0 | 1 | 2 | 1 | 22.77 |
| 38 | V | V | — | VI(LM)(AT) | 4.0 | 0 | 0 | 1 | 23.17 |
| 39 | A | A | P | AS\|T(VG)(CP) | 2.1 | 0 | 2 | 1 | 23.75 |
| 40 | N | N | R | NRHS | 2.9 | 0 | 1 | 1 | 26.09 |
| 41 | D | D | N | DENSQ | 4.1 | 1 | 2 | 1 | 24.68 |
| 42 | Q | Q | S, T | QTESKRN\|DMAP | 1.2 | 0 | 2 | 1 | 21.44 |
| 43 | I | I | S | IVLM\|F(AT)C | 1.7 | 2 | 2 | 2 | 25.76 |
| 44 | K | K | D | KREQNS\|D | 2.7 | 0 | 2 | 3 | 27.98 |
| 45 | T | T | L | TSV\|ANL | 2.6 | 0 | 2 | 1 | 23.97 |
| 46 | F | F | — | FYWILK | 6.0 | 0 | 0 | 1 | 25.47 |
| 47 | V | V | Q | VIML\|(AT)Y | 1.7 | 0 | 2 T45, E49, R31, E4, H7 cover | 1 | 24.30 |
| 48 | A | A | — | ASCGTV | 4.0 | 0 | 0 | 2 | 29.93 |
| 49 | E | E | G | EDQK(SN)\|(RH) | 2.3 | 0 | 2 | 3 | 33.24 |
| 50 | S | S | — | S(TNA)(DEGKQ) | 4.0 | 0 | 0 | 2 | 31.97 |
| 51 | H | N | D | HYN | 3.4 | 1 | 2 | 4 | 40.32 |
| 52 | G | G | — | G(ANS) | 6.0 | 0 | 2 | 2 | 31.85 |
| 53 | F | F | V | PYWI(LM) | 3.2 | 2 | 2 | 1 | 24.44 |
| 54 | M | M | L | MLIVF(Q) | 3.8 | 1 | 2 | 2 | 27.92 |
| 55 | T | T | — | TS(VNA) | 5.0 | 0 | 2 | 1 | 24.25 |
| 56 | G | G | — | G(ANS) | 6.0 | 0 | 1 | 1 | 26.79 |
| 57 | V | T | I | TVI\|LAMSC | 1.9 | 0 | 0 | 2 | 28.35 |
| 58 | E | E | — | EDQK(HNRS) | 5.0 | 0 | 2 | 2 | 27.64 |
| 59 | G | G | — | G(ANS) | 6.0 | 0 | 0 | 1 | 24.40 |
| 60 | I | T | H | TIVL\|M . . . | 0.5 | 0 | 2 | 1 | 24.59 |
| 61 | I | I | — | IVLMF | 4.0 | 0 | 0 | 1 | 23.37 |
| 62 | Y | Y | I | YF(WH) | 3.8 | 0 | 2 | 1 | 25.43 |
| 63 | Y | Y | F | YFWH | 4.9 | 0 | 0 | 2 | 24.79 |
| 64 | S | S | T | STA\|. . . | 2.9 | 0 | 2 | 1 | 25.69 |
| 65 | I | I | V | IVLM | 3.5 | 0 | 0 | 2 | 33.11 |
| 66 | N | N | — | N(DHS)(EKQRT) | 6.0 | 0 | 2 | 5 | 44.24 |
| 67 | G | G | — | G(ANS) | 6.0 | 1 | 2 | 2 | 37.39 |
| 68 | E | E | D | EDQKS\|HR | 3.6 | 0 | 2 | 2 | 34.17 |
| 69 | A | A | I |  | 2.1 | 0 | 0 | 1 | 24.99 |
| 70 | E | E | — |  | 5.0 | 0 | 2 | 2 | 26.75 |
| 71 | I | I | — |  | 4.0 | 0 | 0 | 2 | 25.87 |
| 72 | S | S | T, P |  | 2.3 | 0 | 2 | 1 | 23.17 |
| 73 | L | L | — |  | 4.0 | 0 | 0 | 1 | 21.67 |

APPENDIX 2-continued

PLOTSIMILARITY of: /ul/home/burmeist/projects/binaries/14kD/14kDrops.msf(*) from: 1 to: 133
Window: 1
Scoring matrix: GenRunData: blosum62.cmp
March 28, 2002 15:28
Accessible: 0 < 30%, 1 >= 30%, 2 >= 50%, 3 >= 80%
Out-facing: 0 not, 1 sort of, 2 obvious
B-factor: <=20,

| Position | Consensus | Cry34Ab1 | Obs sub-stitutions (-* invariant) | Sub-stitutions | Similarity Value | Acc | Out-facing | B-factor 0-5 cool to hot | B-factor residue avg from PDB file |
|---|---|---|---|---|---|---|---|---|---|
| 74 | H | Y | | | 4.5 | 0 | 2 | 2 | 24.32 |
| 75 | F | F | — | | 6.0 | 0 | 0 | 1 | 22.92 |
| 76 | D | D | — | | 6.0 | 0 | 2 side-chain coverage | 2 | 20.49 |
| 77 | N | N | — | | 6.0 | 0 | 0 | 0 | 18.23 |
| 78 | P | P | — | | 7.0 | 0 | 2 | 0 | 20.59 |
| 79 | Y | F | | | 6.1 | 1 | 2 | 1 | 22.67 |
| 80 | A | A | I, S | | 0.5 | 1 | 2 | 2 | 28.72 |
| 81 | G | G | — | | 6.0 | 1 | 2 | 2 | 29.78 |
| 82 | S | S | — | | 4.0 | 1 | 2 | 2 | 26.29 |
| 83 | N | N | — | | 6.0 | 0 | 1 x-domain h-bonds | 2 | 25.83 |
| 84 | K | K | — | | 5.0 | 1 | 2 | 3 | 29.80 |
| 85 | Y | Y | C | | 2.7 | 0 | 0 | 2 | 25.28 |
| 86 | D | D | S | | 3.6 | 1 | 2 | 2 | 25.96 |
| 87 | G | G | — | | 6.0 | 0 | 0 | 1 | 26.03 |
| 88 | H | H | R, S, D | | 0.5 | 1 | 2 | 2 | 28.77 |
| 89 | S | S | — | | 4.0 | 0 | 0 | 1 | 24.77 |
| 90 | N | N | D, S | | 2.2 | 1 | 2 | 1 | 21.66 |
| 91 | K | K | D | | 2.7 | 1 | 2 | 2 | 23.44 |
| 92 | P | S | D, N | | 1.5 | 1 | 2 | 0 | 21.69 |
| 93 | Q | Q | E, D | | 2.4 | 1 | 2 | 2 | 27.69 |
| 94 | Y | Y | — | | 7.0 | 0 | 0 | 2 | 24.14 |
| 95 | E | E | K | | 3.4 | 0 | 2 | 4 | 33.40 |
| 96 | V | I | | | 3.8 | 0 | 0 | 1 | 23.34 |
| 97 | I | I | T | | 2.1 | 0 | 2 | 2 | 25.77 |
| 98 | T | T | — | | 5.0 | 0 | 1 | 2 | 26.91 |
| 99 | Q | Q | E | | 3.8 | 1 | 2 | 5 | 34.82 |
| 100 | G | G | S, A | | 1.6 | 0 | 2 | 2 | 28.67 |
| 101 | R | — | | | 0.1 | — | — | — | — |
| 102 | A | — | | | 0.1 | — | — | — | — |
| 103 | E | — | | | 0.1 | — | — | — | — |
| 104 | H | — | | | 0.2 | — | — | — | — |
| 105 | G | G | R | | 2.9 | 0 | 0 | 2 | 30.65 |
| 106 | S | S | A | | 2.8 | 2 | 2 | 2 | 36.17 |
| 107 | G | G | N | | 3.7 | 0 | 2 | 2 | 38.04 |
| 108 | N | N | D | | 3.5 | 0 | 1 | 5 | 41.46 |
| 109 | Q | Q | K, H | | 1.6 | 2 | 2 | 2 | 28.93 |
| 110 | S | S | D | | 2.5 | 0 | 0 | 2 | 28.87 |
| 111 | H | H | — | | 8.0 | 0 | 2 | 2 | 29.45 |
| 112 | V | V | — | | 4.0 | 0 | 0 | 1 | 22.69 |
| 113 | T | T | — | | 5.0 | 0 | 2 | 1 | 24.31 |
| 114 | Y | Y | — | | 7.0 | 0 | 0 | 1 | 22.36 |
| 115 | T | T | — | | 5.0 | 0 | 2 | 1 | 21.19 |
| 116 | I | I | V | | 3.6 | 0 | 0 | 1 | 20.42 |
| 117 | Q | Q | — | | 5.0 | 0 | 2 | 2 | 23.92 |
| 118 | T | T | R | | 2.7 | 1 | 2 | 2 | 24.75 |
| 119 | V | T | N, A | | 0.1 | 0 | 2 | 1 | 23.53 |
| 120 | S | S | I | | 1.7 | 1 | 2 | 1 | 22.14 |
| 121 | S | S | L | | 1.0 | 2 | 2 | 1 | 25.44 |
| 122 | R | R | — | | 5.0 | 2 | 2 | 3 | 31.00 |
| 123 | Y | Y | L | | 2.8 | 3 | 2 | 2 | 26.68 |
| 124 | G | G | *, T | | −1.2 | — | | | |
| 125 | N | H | | | 1.8 | — | | | |
| 126 | N | K | | | 0.9 | — | | | |
| 127 | S | S | L | | 0.3 | — | | | |
| 128 | C | | | | −0.5 | | | | |
| 129 | S | | | | 0.1 | | | | |
| 130 | N | | | | 0.2 | | | | |
| 131 | N | | | | 0.2 | | | | |
| 132 | S | | | | 0.1 | | | | |
| 133 | * | | | | 0.0 | | | | |

The invention claimed is:

1. A truncated Cry34 protein comprising residues 1-114 of a wild-type Cry34 protein and having at least one deletion after residue 114.

2. The truncated Cry34 protein of claim 1 comprising residues 1-118 of said wild-type Cry34 protein.

3. A method of inhibiting a rootworm, wherein said method comprises providing, for ingestion, to said rootworm the protein according to claim 1.

* * * * *